US012619908B2

(12) United States Patent
Lyu

(10) Patent No.: US 12,619,908 B2
(45) Date of Patent: May 5, 2026

(54) SYSTEM AND METHOD FOR MEDICAL IMAGING

(71) Applicant: SHANGHAI UNITED IMAGING HEALTHCARE CO., LTD., Shanghai (CN)

(72) Inventor: Yang Lyu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 1028 days.

(21) Appl. No.: 17/663,417

(22) Filed: May 13, 2022

(65) Prior Publication Data

US 2023/0360794 A1 Nov. 9, 2023

Related U.S. Application Data

(63) Continuation of application No. PCT/CN2022/091671, filed on May 9, 2022.

(51) Int. Cl.
*G06N 20/00* (2019.01)
*G16H 30/20* (2018.01)
*G16H 50/20* (2018.01)

(52) U.S. Cl.
CPC ............. *G06N 20/00* (2019.01); *G16H 30/20* (2018.01); *G16H 50/20* (2018.01)

(58) Field of Classification Search
None
See application file for complete search history.

(56) References Cited

U.S. PATENT DOCUMENTS

2015/0363948 A1* 12/2015 Leahy ................... A61B 6/504
600/425
2019/0104940 A1 4/2019 Zhou et al.
(Continued)

FOREIGN PATENT DOCUMENTS

CN 110363288 A 10/2019
CN 110458778 A 11/2019
(Continued)

OTHER PUBLICATIONS

Schmitz, Ruth E., Robert L. Harrison, Charles W. Stearns, Thomas K. Lewellen, and Paul E. Kinahan. "Optimization of noise equivalent count rate performance for a partially collimated PET scanner by varying the number of septa." IEEE Transactions on Medical Imaging 26, No. 7 (2007): 935-944. (Year: 2007).*
(Continued)

*Primary Examiner* — Vincent Gonzales
(74) *Attorney, Agent, or Firm* — METIS IP LLC

(57) ABSTRACT
The present disclosure provides a medical imaging system and method. The method may include obtaining a machine learning model and preliminary training data of at least one sample subject.
The method may also include generating training input data by processing the preliminary training data, the preliminary training data being superior to the training input data with respect to a data quality parameter. The method may further include determining a trained machine learning model by training the machine learning model based on the training input data and the preliminary training data, the preliminary training data being configured as training target data of the machine learning model.

20 Claims, 11 Drawing Sheets

(56)                    References Cited

U.S. PATENT DOCUMENTS

| | | |
|---|---|---|
| 2019/0365341 A1 | 12/2019 | Chan et al. |
| 2020/0065940 A1 | 2/2020 | Tang et al. |
| 2020/0289077 A1 | 9/2020 | Bai et al. |
| 2020/0311914 A1 | 10/2020 | Zaharchuk et al. |
| 2021/0052233 A1 | 2/2021 | Kaplan et al. |
| 2022/0261965 A1 | 8/2022 | Ji et al. |

FOREIGN PATENT DOCUMENTS

| | | |
|---|---|---|
| CN | 112308785 A | 2/2021 |
| CN | 111325686 B | 3/2021 |
| CN | 112508175 A | 3/2021 |
| WO | 2020239506 A1 | 12/2020 |

OTHER PUBLICATIONS

Gondara, Lovedeep. "Medical image denoising using convolutional denoising autoencoders." In 2016 IEEE 16th international conference on data mining workshops (ICDMW), pp. 241-246. IEEE, 2016. (Year: 2016).*
Onishi, Yuya, Fumio Hashimoto, Kibo Ote, Hiroyuki Ohba, Ryosuke Ota, Etsuji Yoshikawa, and Yasuomi Ouchi. "Anatomical-guided attention enhances unsupervised PET image denoising perfor-mance." Medical image analysis 74 (2021): 102226. 13 pages. (Year: 2021).*
Zaidi, Habib, and Issam El Naqa. "Quantitative molecular positron emission tomography imaging using advanced deep learning tech-niques." Annual review of biomedical engineering 23, No. 1 (2021): 249-276. (Year: 2021).*
The Communication Pursuant to Article 94(3) EPC in European Application No. 22941025.3 mailed on Apr. 10, 2025, 6 pages.
Amirhossein Sanaat et al., Time-Of Flight (TOF) Image Synthesis From Non-TOF PET Using Deep Learning, 2021 IEEE Nuclear Science Symposium And Medical Imaging Conference, 2021, 2 pages.
International Search Report in PCT/CN2022/091671 mailed on Dec. 26, 2022, 5 pages.
Written Opinion in PCT/CN2022/091671 mailed on Dec. 26, 2022, 4 pages.
Lv, Yang et al., PET image reconstruction with deep progressive learning, Physics in Medicine & Biology, 2021, 13 pages.
Wang, Taisong et al., Can a Deep Progressive Learning Method Help to Achieve High Image Quality as Total-body PET Imaging?, Research Square, 2021, 25 pages.
Lan, Xiaoli et al., First clinical experience of 106 cm, long axial field-of-view (LAFOV) PET/CT: an elegant balance between stan-dard axial (23 cm) and total-body (194 cm) systems, European Journal of Nuclear Medicine and Molecular Imaging, 2021, 5 pages.
The Extended European Search Report in European Application No. 22941025.3 mailed on Jun. 5, 2024, 7 pages.

* cited by examiner

300

<u>500</u>

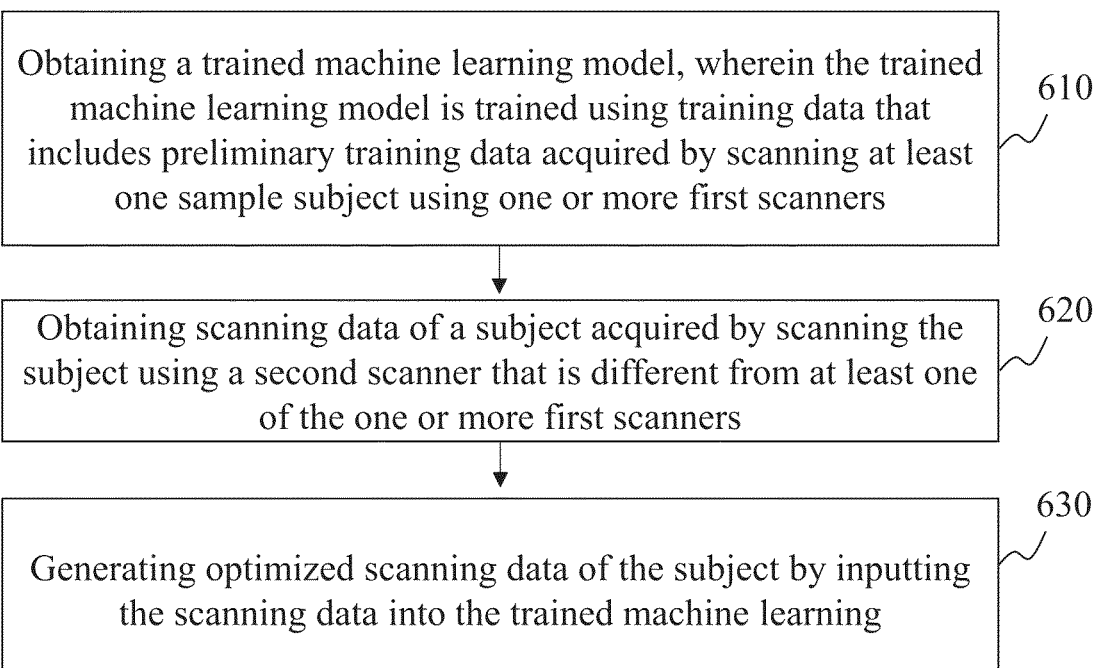

<u>600</u>

Obtaining a trained machine learning model, wherein the trained machine learning model is trained using training data that includes preliminary training data acquired by scanning at least one sample subject using one or more first scanners  610

Obtaining scanning data of a subject acquired by scanning the subject using a second scanner that is different from at least one of the one or more first scanners  620

Generating optimized scanning data of the subject by inputting the scanning data into the trained machine learning  630

FIG. 6

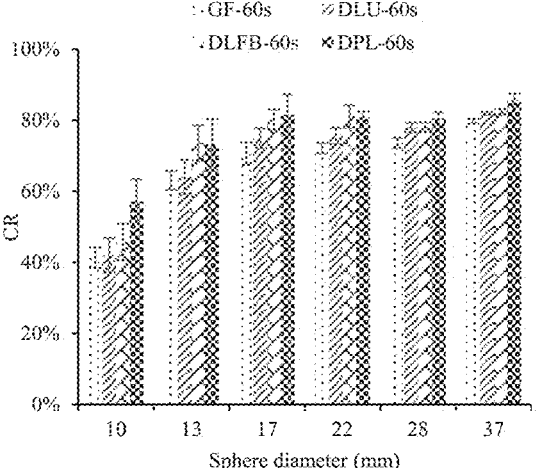
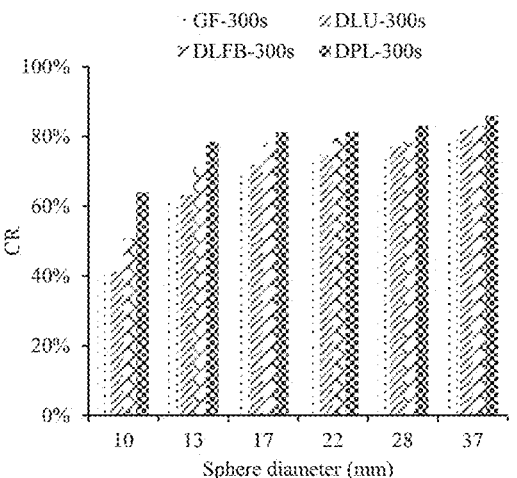
FIG. 8A
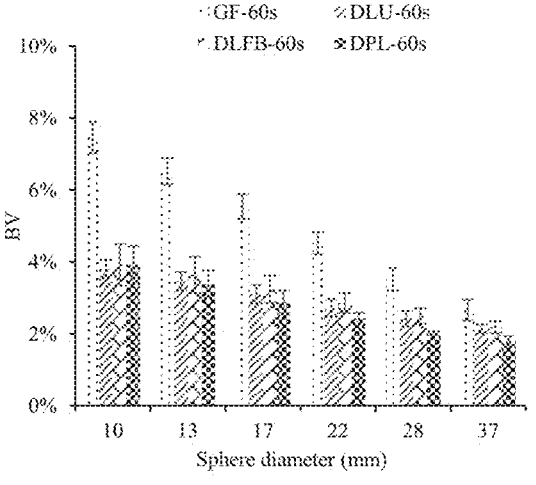
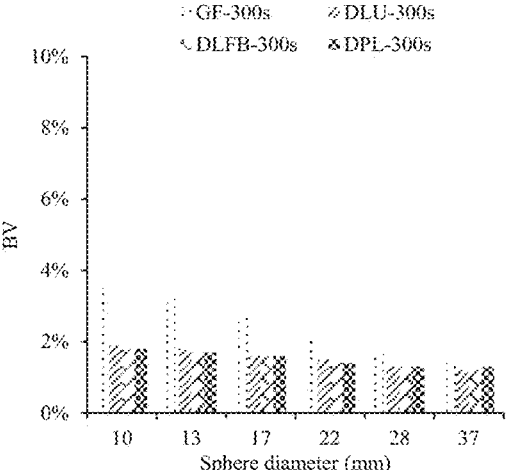
FIG. 8B

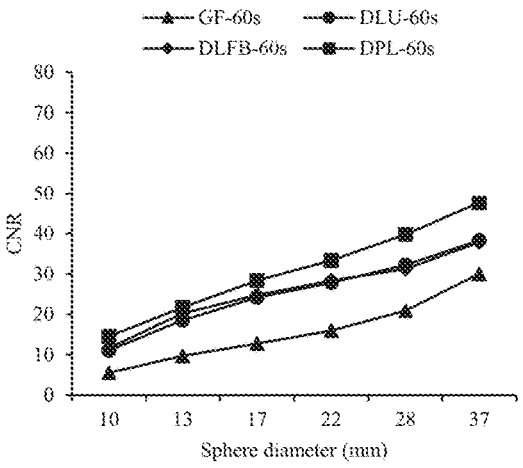
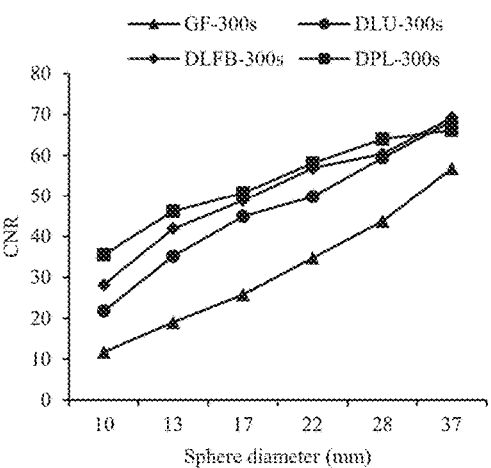
FIG. 8C
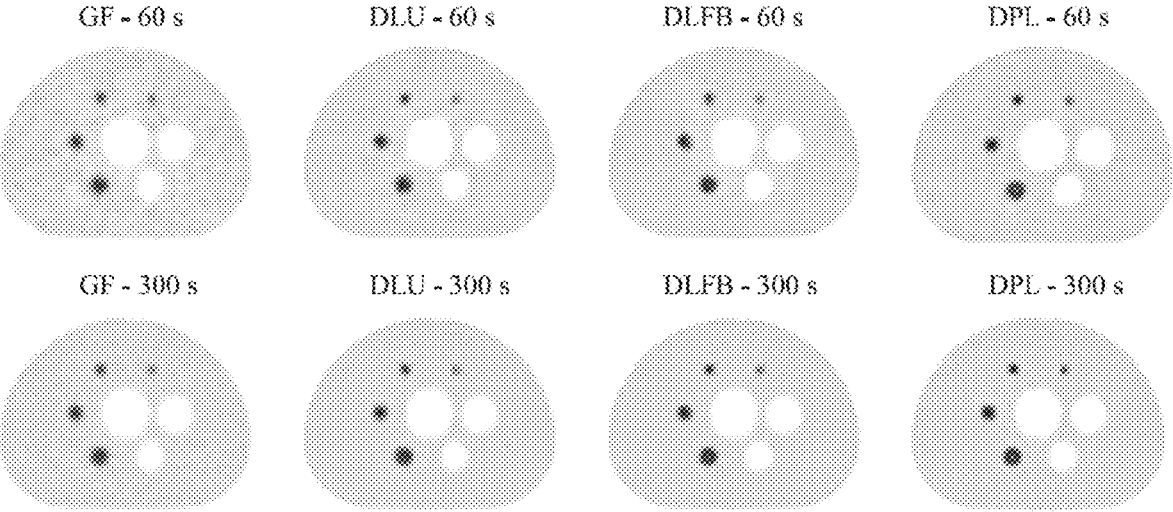
FIG. 9

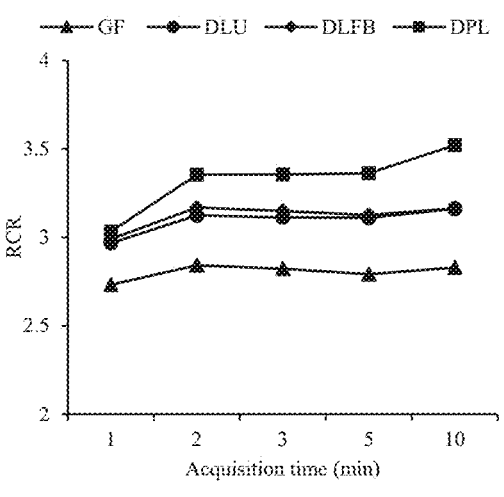
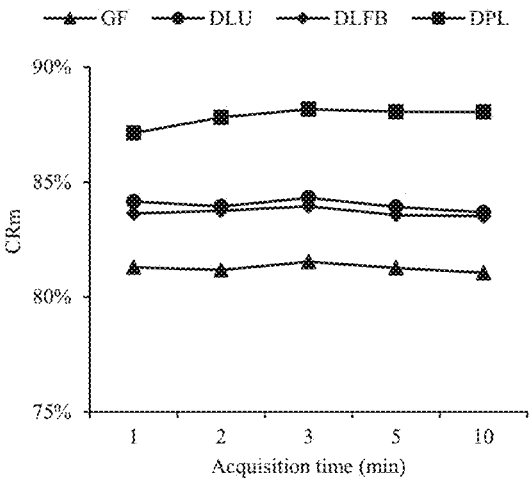
FIG. 10A                                        FIG. 10B
FIG. 11

SYSTEM AND METHOD FOR MEDICAL IMAGING

CROSS-REFERENCE TO RELATED APPLICATIONS

This application claims priority to International Patent Application No. PCT/CN2022/091671, filed on May 9, 2022, the content of which is hereby incorporated by reference.

TECHNICAL FIELD

The present disclosure generally relates to systems and methods for medical imaging, and more particularly, to systems and methods for data and/or image optimization in medical imaging.

BACKGROUND

At present, machine learning models (e.g., a neural network model) are widely used for data and/or image optimization in medical imaging. For example, a deep neural network may be used for image denoising and/or enhancement so as to improve the efficiency and accuracy of disease diagnosis and/or treatment. A machine learning model may be trained using training data including training input data and training target data, which servers as a target or reference of the output of the machine learning model. The quality of data and/or images output from the machine learning model is ultimately dependent upon the quality of the training data (e.g., the training target data). Conventionally, training data of high quality is obtained by prolonging a scanning time of a subject, increasing a dose of medicine injected into the subject, and/or improving a time-of-flight (TOF) sensitivity of an imaging system used for scanning the subject. However, the conventional methods may increase a radiation dose of the subject, be more susceptible to motion artifact and increase discomfort of the subject due to, e.g., a prolonged scanning time, and/or have a limited improvement on the quality of the training data. Thus, it is desirable for a system and method for providing training data of high quality effectively and conveniently.

SUMMARY

According to one aspect of the present disclosure, a system is provided. The system may comprise at least one storage medium including a set of instructions; and at least one processor configured to communicate with the at least one storage medium. When executing the set of instructions, the at least one processor is configured to direct the system to perform operations including obtaining a machine learning model and preliminary training data of at least one sample subject; generating training input data by processing the preliminary training data, the preliminary training data being superior to the training input data with respect to a data quality parameter; and determining a trained machine learning model by training the machine learning model based on the training input data and the preliminary training data, the preliminary training data being configured as training target data of the machine learning model.

In some embodiments, the preliminary training data includes at least one of raw data obtained from one or more first scanners, sinogram data corresponding to the raw data, or image data reconstructed based on the raw data.

In some embodiments, the data quality parameter includes at least one of a signal-to-noise ratio (SNR), a spatial resolution, or an image contrast.

In some embodiments, the preliminary training data is processed by performing at least one of a data splitting operation, a data rebinning operation, or a down-sampling operation.

In some embodiments, the preliminary training data includes first scanning data generated by a first positron emission tomography (PET) scanner having an axial length exceeding a threshold axial length.

In some embodiments, the generating training input data by processing the preliminary training data includes: down-sampling the first scanning data at a preset down-sampling rate; and designating the down-sampled first scanning data as the training input data.

In some embodiments, the preliminary training data includes first listmode data generated by a first PET scanner having a time of flight (TOF) resolution exceeding a threshold TOF resolution.

In some embodiments, the generating training input data by processing the preliminary training data includes: rebinning the first listmode data according to preset TOF information, a TOF resolution corresponding to the preset TOF information being below the threshold TOF resolution; and designating the rebinned first listmode data as the training input data.

In some embodiments, the preliminary training data includes second listmode data generated by a first PET scanner having a detector unit size being below a threshold detector unit size.

In some embodiments, the generating training input data by processing the preliminary training data includes: determining coordinates of virtual detector units based on coordinates of detector units of the first PET scanner and a preset detector unit size, the preset detector unit size exceeding the threshold detector unit size; rebinning the second listmode data according to the determined coordinates of the virtual detector units; and designating the rebinned second listmode data as the training input data.

In some embodiments, preliminary training data includes third listmode data generated by a first PET scanner having a noise equivalent count rate (NECR) exceeding a threshold NECR.

In some embodiments, the generating training input data by processing the preliminary training data includes: extracting a data set from delayed coincidence counts of the third listmode data; generating two data sets by duplicating the data set, wherein coincidence marks of one data set remain unchanged, and coincidence marks of the other data set are replaced with prompt coincidence counts; generating fourth listmode data by incorporating the two data sets into the third listmode data; and designating the fourth listmode data as the training input data.

In some embodiments, the trained machine learning model is configured to generate optimized second scanning data of a subject by inputting into the trained machine learning model second scanning data that are acquired by scanning the subject using a second scanner.

According to another aspect of the present disclosure, a system is provided. The system may comprise at least one storage medium including a set of instructions; and at least one processor configured to communicate with the at least one storage medium. When executing the set of instructions, the at least one processor is configured to direct the system to perform operations including obtaining a trained machine learning model, wherein the trained machine learning model is trained using training data that includes preliminary training data acquired by scanning at least one sample subject using one or more first scanners; obtaining scanning data of a subject acquired by scanning the subject using a second scanner that is different from at least one of the one or more first scanners; and generating optimized scanning data of the subject by inputting the scanning data into the trained machine learning.

In some embodiments, the optimized scanning data is superior to the scanning data with respect to a data quality parameter.

In some embodiments, the data quality parameter includes at least one of a signal-to-noise ratio (SNR), a spatial resolution, or an image contrast.

In some embodiments, the trained machine learning model is trained by: generating training input data by processing the preliminary training data, the preliminary training data being superior to the training input data with respect to a data quality parameter; and determining the trained machine learning model by training the machine learning model based on the training input data and the preliminary training data, the preliminary training data being configured as training target data of the machine learning model.

In some embodiments, the preliminary training data includes at least one of raw data obtained from one or more first scanners, sinogram data corresponding to the raw data, or image data reconstructed based on the raw data.

According to a further aspect of the present disclosure, a method is provided. The method may be implemented on a computing device having a processor and a computer-readable storage device. The method may comprise obtaining a machine learning model and preliminary training data of at least one sample subject; generating training input data by processing the preliminary training data, the preliminary training data being superior to the training input data with respect to a data quality parameter; and determining a trained machine learning model by training the machine learning model based on the training input data and the preliminary training data, the preliminary training data being configured as training target data of the machine learning model.

According to a further aspect of the present disclosure, a method is provided. The method may be implemented on a computing device having a processor and a computer-readable storage device. The method may comprise obtaining a trained machine learning model, wherein the trained machine learning model is trained using training data that includes preliminary training data acquired by scanning at least one sample subject using one or more first scanners; obtaining scanning data of a subject acquired by scanning the subject using a second scanner that is different from at least one of the one or more first scanners; and generating optimized scanning data of the subject by inputting the scanning data into the trained machine learning.

According to a further aspect of the present disclosure, a non-transitory readable medium including at least one set of instructions is provided. When executed by at least one processor of a computing device, the at least one set of instructions may direct the at least one processor to perform a method. The method may include obtaining a machine learning model and preliminary training data of at least one sample subject; generating training input data by processing the preliminary training data, the preliminary training data being superior to the training input data with respect to a data quality parameter; and determining a trained machine learning model by training the machine learning model based on the training input data and the preliminary training data, the preliminary training data being configured as training target data of the machine learning model.

According to a further aspect of the present disclosure, a non-transitory readable medium including at least one set of instructions is provided. When executed by at least one processor of a computing device, the at least one set of instructions may direct the at least one processor to perform a method. The method may include obtaining a trained machine learning model, wherein the trained machine learning model is trained using training data that includes preliminary training data acquired by scanning at least one sample subject using one or more first scanners; obtaining scanning data of a subject acquired by scanning the subject using a second scanner that is different from at least one of the one or more first scanners; and generating optimized scanning data of the subject by inputting the scanning data into the trained machine learning.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 6 includes a flowchart illustrating an exemplary process for generating optimized scanning data of a subject according to some embodiments of the present disclosure;

FIGS. 8A-8C illustrate exemplary diagrams of contrast recoveries, background variations and contrast to noise ratios of images of an international electrotechnical commission (IEC) body phantom reconstructed based on simulated fast scan data and full data according to different approaches according to some embodiments of the present disclosure;

5

Figures 12, 13:
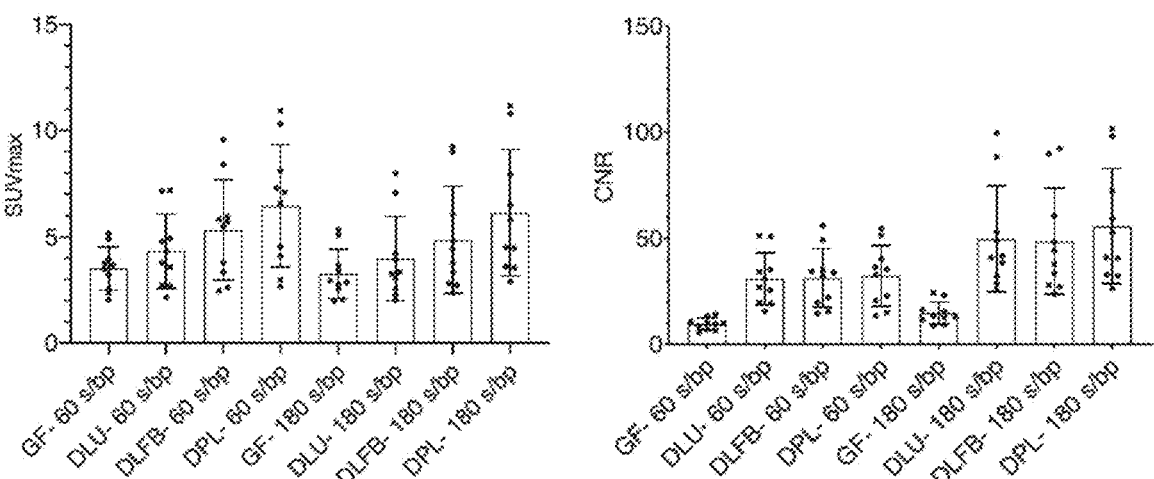

FIG. 9 illustrates images of an IEC body phantom reconstructed using simulated fast scan data and full data according to different approaches according to some embodiments of the present disclosure;

FIGS. 10A and 10B illustrate exemplary diagrams of radioactivity concentration ratios and contrast recoveries of images of a Hoffman brain phantom generated based on simulated fast scan data and full data according to different approaches according to some embodiments of the present disclosure;

FIG. 11 illustrates images of the Hoffman brain phantom reconstructed based on scanning data corresponding to different scanning time periods according to different approaches according to some embodiments of the present disclosure;

FIG. 12 illustrates images of a patient reconstructed based on full data and fast scan data according to different approaches according to some embodiments of the present disclosure; and FIG. 13 illustrates maximum standardized uptake values and contrast to noise ratios of the lesions in images reconstructed based on full data and fast scan data according to the different approaches according to some embodiments of the present disclosure.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

It will be understood that the term "system," "engine," "unit," "module," and/or "block" used herein are one method to distinguish different components, elements, parts, section or assembly of different level in ascending order. However, the terms may be displaced by another expression if they may achieve the same purpose.

Figure 2:
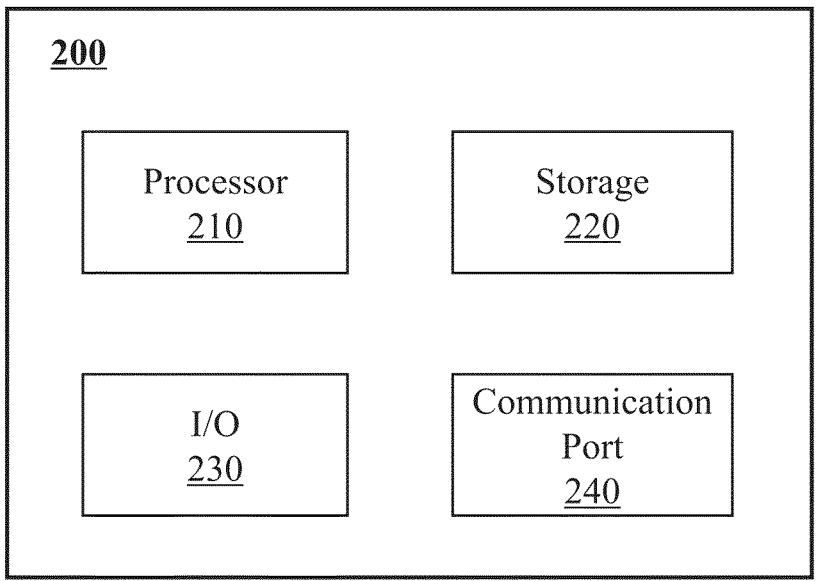
FIG. 2 is a schematic diagram illustrating hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on a computing device (e.g., processor 210 as illustrated in FIG. 2) may be provided on a computer readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing apparatus, for execution by the computing apparatus. Software instructions may be embedded in firmware, such as an erasable programmable read-only memory (EPROM). It will be further appreciated that hardware modules/units/blocks may be included of connected logic components, such as gates and flip-flops, and/or can be included of programmable units, such as programmable gate arrays or processors. The modules/units/blocks or computing apparatus functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to" another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include" and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

The flowcharts used in the present disclosure illustrate operations that systems implement according to some embodiments of the present disclosure. It is to be expressly understood the operations of the flowcharts may be implemented not in order. Conversely, the operations may be implemented in an inverted order, or simultaneously. Moreover, one or more other operations may be added to the flowcharts. One or more operations may be removed from the flowcharts.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and methods for non-invasive imaging, such as for disease diagnosis, treatment, and/or research purposes. In some embodiments, the imaging system may include a single modality system and/or a multi-modality system. The term "modality" used herein broadly refers to an imaging or treatment method or technology that gathers, generates, processes, and/or analyzes imaging information of a subject or treatments the subject. The single modality system may include a positron emission tomography (PET) system, a computed tomography (CT) system, a magnetic resonance imaging (MRI) system, an ultrasound imaging system, an X-ray imaging system, an ultrasonography system, an optical coherence tomography (OCT) imaging system, an ultrasound (US) imaging system, an intravascular ultrasound (IVUS) imaging system, a near-infrared spectroscopy (NIRS) imaging system, or the like, or any combination thereof. The multi-modality system may include a positron emission tomography-computed tomography (PET-CT) system, a positron emission tomography-magnetic resonance imaging (PET-MR) system, a positron emission tomography-X-ray imaging (PET-X-ray) system, a single-photon emission computed tomography-magnetic resonance imaging (SPECT-MRI) system, an X-ray imaging-magnetic resonance imaging (X-ray-MRI) system, a digital subtraction angiography-magnetic resonance imaging (DSA-MRI) system, or the like, or any combination thereof.

In the present disclosure, the term "image" refers to a two-dimensional (2D) image, a three-dimensional (3D) image, or a four-dimensional (4D) image. In some embodiments, the term "image" refers to an image of a region (e.g., a region of interest (ROI)) of a subject. As described above, the image may be a PET image, a CT image, an MR image, a fluoroscopy image, an ultrasound image, etc.

As used herein, a representation of a subject (e.g., a patient, or a portion thereof) in an image may be referred to as the subject for brevity. For instance, a representation of an organ or tissue (e.g., the heart, the liver, a lung, etc., of a patient) in an image may be referred to as the organ or tissue for brevity. An image including a representation of a subject may be referred to as an image of the subject or an image including the subject for brevity. As used herein, an operation on a representation of a subject in an image may be referred to as an operation on the subject for brevity. For instance, a segmentation of a portion of an image including a representation of an organ or tissue (e.g., the heart, the liver, a lung, etc., of a patient) from the image may be referred to as a segmentation of the organ or tissue for brevity.

According to an aspect of the present disclosure, a machine learning model and preliminary training data of at least one sample subject may be obtained. Training data including training input data and training target data may be generated for training the machine learning model. The training input data may be generated by processing the preliminary training data (e.g., by splitting, rebinning, and/or down-sampling the preliminary training data). The preliminary training data may be superior to the training input data with respect to a data quality parameter. The preliminary training data may be configured as the training target data. The machine learning model may be trained based on the training input data and the training target data. In this way, training data of high quality may be obtained, and the machine learning model may be trained based on the training data of high quality, and optimized data and/or images may be generated by inputting scanning data of a subject into the trained machine learning model. Thus, the data and/or image optimization may be realized.

In some embodiments, a trained machine learning model may be determined by training using training data including scanning data acquired using a long-axis PET scanner. For instance, the length of the FOV of the long-axis PET scanner may be 1 meter, 1.5 meters, etc. Merely by way of example, the long-axis PET scanner may be a total-body PET scanner. The trained machine learning model may be configured to provide optimized PET scanning data or optimized PET image(s) based on scanning data acquired in a PET scan of a subject using a regular PET scanner. For instance, the length of the FOV of the regular PET scanner may be shorter than 1 meter, 1.5 meters, etc. In some embodiments, by the optimization using the trained machine learning model which is trained based on the preliminary training data, the optimized PET scanning data or optimized PET image(s) may achieve or approach the quality that corresponds to data acquired using the long-axis PET scanner, thereby obviating the need to extend the scan time of the PET scan using the regular PET scanner, increase the dosage of the radiotracer intaken by the subject for the PET scan, and/or use a PET scanner of a better configuration (e.g., higher TOF resolution).

Figure 1:
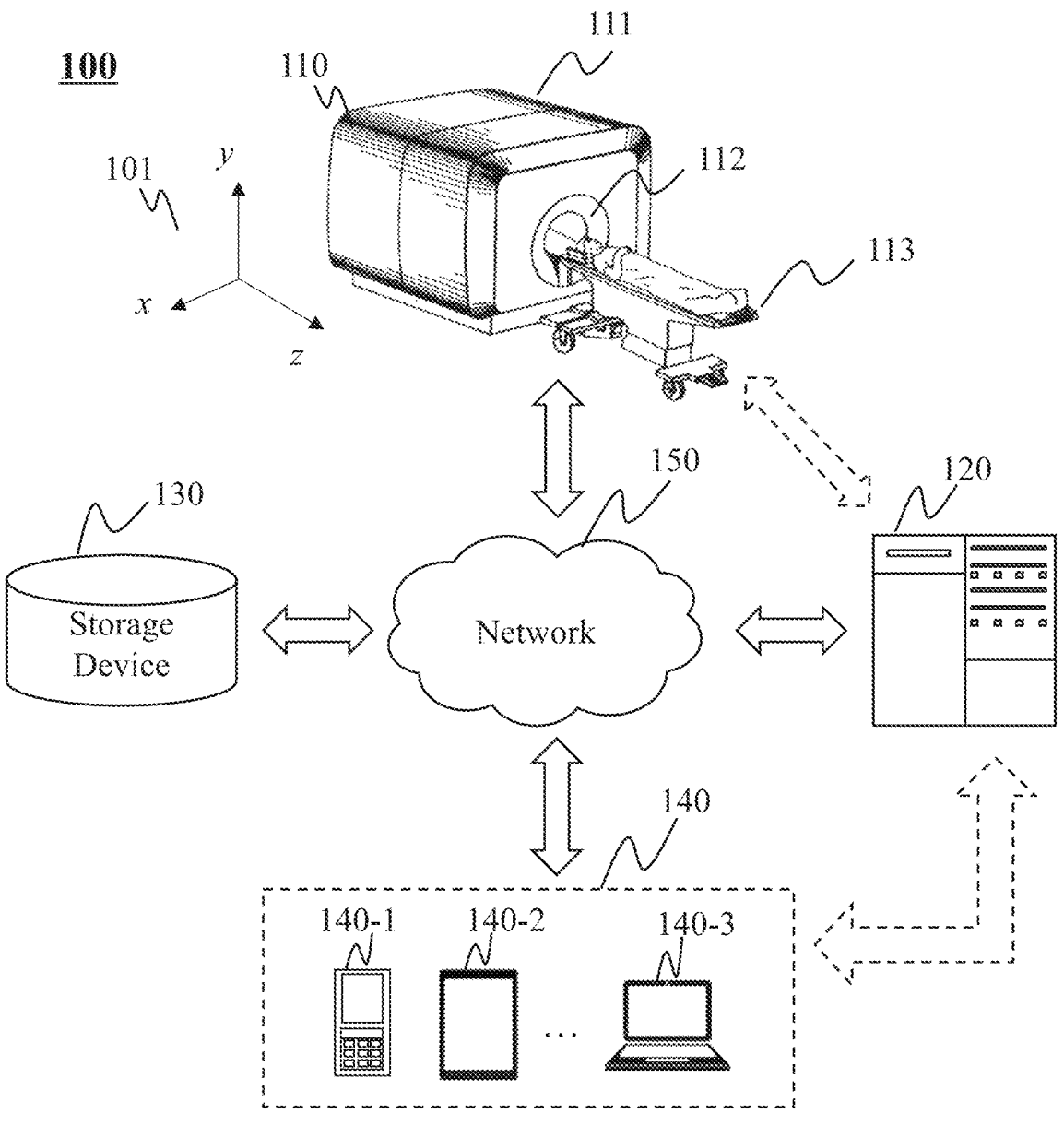
FIG. 1 is a schematic diagram illustrating an exemplary imaging system according to some embodiments of the present disclosure.

FIG. 1 is a schematic diagram illustrating an exemplary imaging system 100 according to some embodiments of the present disclosure. As illustrated, the imaging system 100 may include a scanner 110, a processing device 120, a storage device 130, one or more terminals 140, and a network 150. The components in the imaging system 100 may be connected in various ways. Merely by way of example, as illustrated in FIG. 1, the scanner 110 may be connected to the processing device 120 through the network 150. As another example, the scanner 110 may be connected with the processing device 120 directly as indicated by the bi-directional arrow in dotted lines linking the scanner 110 and the processing device 120. As a further example, the storage device 130 may be connected with the processing device 120 directly (not shown in FIG. 1) or through the network 150. As still a further example, one or more terminal(s) 140 may be connected with the processing device 120 directly (as indicated by the bi-directional arrow in dotted lines linking the terminal(s) 140 and the processing device 120) or through the network 150.

For illustration purposes, a coordinate system 101 including an x-axis, a y-axis, and a z-axis is provided in FIG. 1. The x-axis and the z-axis shown in FIG. 1 may be horizontal, and the y-axis may be vertical. As illustrated, the positive x direction along the x-axis may be from the right side to the left side of the scanner 110 seen from the direction facing the front of the scanner 110; the positive y direction along the y-axis shown in FIG. 1 may be from the lower part to the upper part of the scanner 110; the positive z direction along the z-axis shown in FIG. 1 may refer to a direction in which a subject is moved out of the scanning channel (or referred to as the bore) of the scanner 110.

The scanner 110 may scan a subject or a portion thereof that is located within its detection region, and generate scanning data relating to the (portion of) subject. The scanner 110 may include a positron emission computed tomography (PET) scanner, a single-photon emission computed tomography (SPECT) scanner, an emission computed tomography (ECT) scanner, a computed tomography (CT) scanner, or the like. In some embodiment, the scanner 110 may be a multi-modality device including two or more scanners exemplified above. For example, the scanner 110 may be a PET-CT scanner, a PET-MR scanner, etc. The following descriptions are provided, unless otherwise stated expressly, with reference to a PET scanner for illustration purposes and not intended to be limiting.

The PET scanner may include a gantry 111, a detecting region 112, and a scanning bed 113. The gantry 111 may support one or more detectors (not shown). A subject may be placed on the scanning bed 113 for a PET scan.

To prepare for a PET scan, a radionuclide (also referred to as "PET tracer" or "PET tracer molecules") may be introduced into the subject. The PET tracer may emit positrons in the detecting region 112 when it decays. An annihilation (also referred to as "annihilation event" or "coincidence event") may occur when a positron collides with an electron. The annihilation may produce two photons (e.g., gamma photons), which may travel in opposite directions. A line connecting detector units that detecting the two gamma photons may be defined as a "line of response (LOR)." One or more detectors set on the gantry 111 may detect the coincidence events (e.g., gamma photons) emitted from the detecting region 112. The coincidence events emitted from the detecting region 112 may be detected and used to generate PET data (also referred to as scanning data). In some embodiments, the one or more detectors used in the PET scan may include crystal elements and photomultiplier tubes (PMT).

The processing device 120 may process data and/or information obtained and/or retrieve from the scanner 110, the terminal(s) 140, the storage device 130 and/or other storage devices. For example, the processing device 120 may obtain preliminary training data of at least one sample subject, generate training input data by processing the pre-liminary training data, and determining a trained machine learning model by training a machine learning model based on the training input data and the preliminary training data. As another example, the processing device 120 may obtain scanning data of a subject from the scanner 110, and generating optimized scanning data of the subject by input-ting the scanning data into a trained machine learning model. As a further example, the processing device 120 may reconstruct an image of the subject based on the optimized scanning data. In some embodiments, the processing device 120 may be a single server or a server group. The server group may be centralized or distributed. In some embodi-ments, the processing device 120 may be local or remote. For example, the processing device 120 may access infor-mation and/or data stored in the scanner 110, the terminal(s) 140, and/or the storage device 130 via the network 150. As another example, the processing device 120 may be directly connected with the scanner 110, the terminal(s) 140, and/or the storage device 130 to access stored information and/or data. In some embodiments, the processing device 120 may be implemented on a cloud platform. Merely by way of example, the cloud platform may include a private cloud, a public cloud, a hybrid cloud, a community cloud, a distrib-uted cloud, an inter-cloud, a multi-cloud, or the like, or any combination thereof. In some embodiments, the processing device 120 may be implemented on a computing device 200 having one or more components illustrated in FIG. 2 in the present disclosure.

The storage device 130 may store data and/or instructions. In some embodiments, the storage device 130 may store data obtained from the scanner 110, the terminal(s) 140, and/or the processing device 120. For example, the storage device 130 may store scanning data, signals, images, algorithms, texts, instructions, program codes, etc. In some embodi-ments, the storage device 130 may store data and/or instruc-tions that the processing device 120 may execute or use to perform exemplary methods described in the present disclo-sure. In some embodiments, the storage device 130 may include a mass storage device, a removable storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memories may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected with the network 150 to communicate with one or more components of the imaging system 100 (e.g., the processing device 120, the terminal(s) 140, etc.). One or more components of the imaging system 100 may access the data or instructions stored in the storage device 130 via the network 150. In some embodiments, the storage device 130 may be directly connected or communicate with one or more components of the imaging system 100 (e.g., the processing device 120, the terminal(s) 140, etc.). In some embodiments, the storage device 130 may be part of the processing device 120.

The terminal(s) 140 may include a mobile device 140-1, a tablet computer 140-2, a laptop computer 140-3, or the like, or any combination thereof. In some embodiments, a terminal 140 may be used to perform one or more tasks including, e.g., at least a portion of image reconstruction, providing user data of a user (e.g., the weight of the patient, the height of the patient, the age of the patient, etc.), presentation of at least one image or relevant data, facili-tating user interaction with one or more other component of the imaging system 100, etc. In some embodiments, the mobile device 140-1 may include a smart home device, a wearable device, a smart mobile device, a virtual reality device, an augmented reality device, or the like, or any combination thereof. In some embodiments, the smart home device may include a control device of an intelligent elec-tronic apparatus, a smart monitoring device, a smart televi-sion, a smart video camera, an interphone, or the like, or any combination thereof. In some embodiments, the wearable device may include a smart bracelet, smart footgear, a pair of smart glasses, a smart helmet, a smartwatch, smart clothing, a smart backpack, a smart accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google Glass, an Oculus Rift, a Hololens, a Gear VR, etc. In some embodi-ments, the terminal(s) 140 may remotely operate the scanner 110. In some embodiments, the terminal(s) 140 may operate the scanner 110 via a wireless connection. In some embodi-ments, the terminal(s) 140 may receive information and/or instructions inputted by a user, and send the received infor-mation and/or instructions to the scanner 110 or the pro-cessing device 120 via the network 150. In some embodiments, the terminal(s) 140 may receive data and/or information from the processing device 120. In some embodiments, the terminal(s) 140 may be part of the processing device 120. In some embodiments, the terminal(s) 140 may be omitted.

The network 150 may include any suitable network that can facilitate the exchange of information and/or data for the imaging system 100. In some embodiments, one or more components of the imaging system 100 (e.g., the scanner 110, the terminal(s) 140, the processing device 120, or the storage device 130) may communicate information and/or data with one or more other components of the imaging system 100 via the network 150. In some embodiments, the network 150 may be any type of wired or wireless network, or a combination thereof. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a Zig-Bee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the imaging system 100 may be connected with the network 150 to exchange data and/or information.

It should be noted that the above description of the imaging system 100 is merely provided for the purposes of illustration, not intended to limit the scope of the present disclosure. For persons having ordinary skills in the art, components contained in the imaging system 100 may be combined or adjusted in various ways, or connected with other components as sub-systems, and various variations and modifications may be conducted under the teaching of the present disclosure. However, those variations and modifications may not depart the spirit and scope of this disclosure. For example, the scanner 110 may be a standalone device external to the imaging system 100, and the imaging system 100 may be connected to or in communication with the scanner 110 via the network 150. All such modifications are within the protection scope of the present disclosure.

FIG. 2 is a schematic diagram illustrating hardware and/or software components of an exemplary computing device 200 on which the processing device 120 may be implemented according to some embodiments of the present disclosure. As illustrated in FIG. 2, the computing device 200 may include a processor 210, storage 220, an input/output (I/O) 230, and a communication port 240.

The processor 210 may execute computer instructions (program code) and perform functions of the processing device 120 in accordance with techniques described herein. The computer instructions may include, for example, routines, programs, objects, components, signals, data structures, procedures, modules, and functions, which perform particular functions described herein. For example, the processor 210 may process data obtained from the scanner 110, the terminal(s) 140, the storage device 130, and/or any other component of the imaging system 100. Specifically, the processor 210 may process scanning data obtained from the scanner 110. For example, the processor 210 may generate an image based on the scanning data. In some embodiments, the image may be stored in the storage device 130, the storage 220, etc. In some embodiments, the image may be displayed on a display device by the I/O 230. In some embodiments, the processor 210 may perform instructions obtained from the terminal(s) 140. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the scanner 110, the terminal(s) 140, the storage device 130, or any other component of the imaging system 100. In some embodiments, the storage 220 may include a mass storage device, a removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 120 for reducing noise in an image.

The I/O 230 may input or output signals, data, and/or information. In some embodiments, the I/O 230 may enable user interaction with the processing device 120. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected with a network (e.g., the network 150) to facilitate data communications. The communication port 240 may establish connections between the processing device 120 and the scanner 110, the terminal(s) 140, or the storage device 130. The connection may be a wired connection, a wireless connection, or a combination of both that enables data transmission and reception. The wired connection may include an electrical cable, an optical cable, a telephone wire, or the like, or any combination thereof. The wireless connection may include Bluetooth, Wi-Fi, WiMax, WLAN, ZigBee, mobile network (e.g., 3G, 4G, 5G, etc.), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
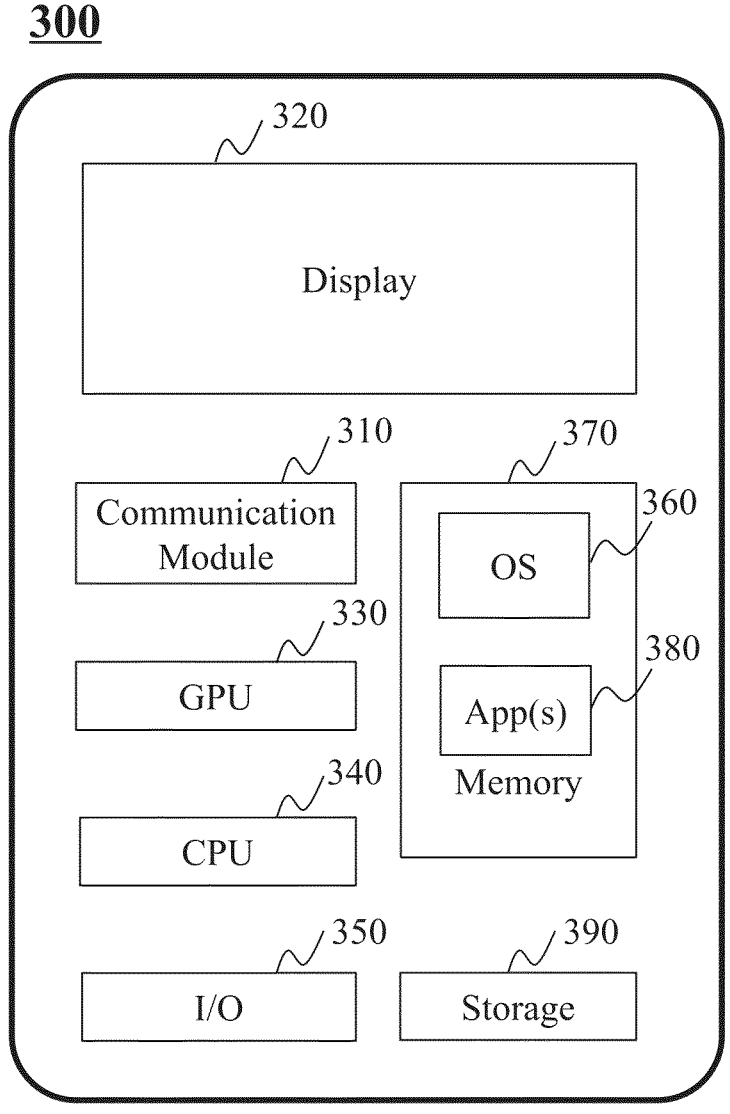
FIG. 3 is a schematic diagram illustrating hardware and/or software components of an exemplary mobile device according to some embodiments of the present disclosure.

FIG. 3 is a schematic diagram illustrating hardware and/or software components of an exemplary mobile device 300 according to some embodiments of the present disclosure. As illustrated in FIG. 3, the mobile device 300 may include a communication module 310, a display 320, a graphics processing unit (GPU) 330, a central processing unit (CPU) 340, an I/O 350, a memory 370, and storage 390. In some embodiments, any other suitable component, including but not limited to a system bus or a controller (not shown), may also be included in the mobile device 300. In some embodiments, a mobile operating system 360 (e.g., iOS, Android, Windows Phone, etc.) and one or more applications 380 may be loaded into the memory 370 from the storage 390 in order to be executed by the CPU 340. The applications 380 may include a browser or any other suitable mobile apps for receiving and rendering information relating to data processing or other information from the processing device 120. User interactions with the information stream may be achieved via the I/O 350 and provided to the processing device 120 and/or other components of the imaging system 100 via the network 150.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to generate an imaging report as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 4:
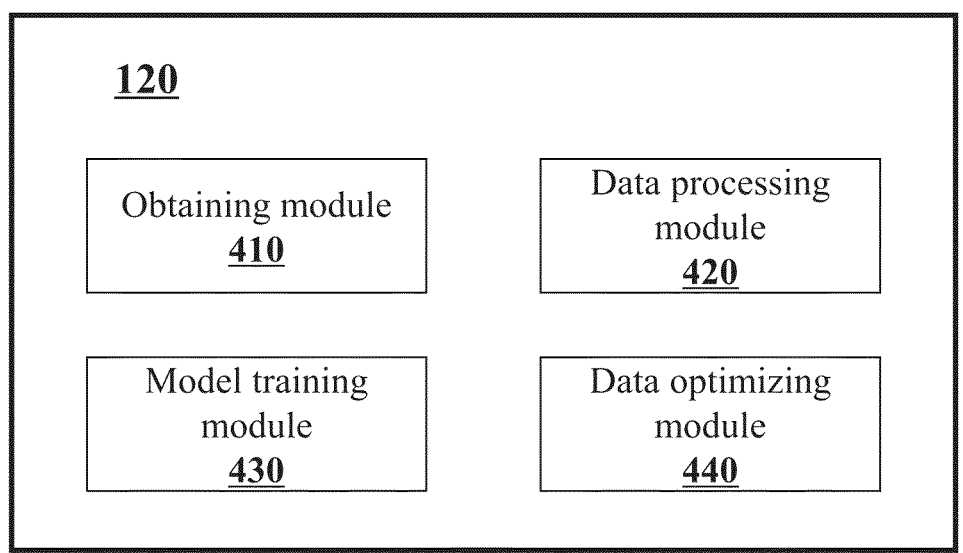
FIG. 4 is a block diagram illustrating an exemplary processing device according to some embodiments of the present disclosure.

FIG. 4 is a block diagram illustrating an exemplary processing device according to some embodiments of the present disclosure. The processing device 120 may include an obtaining module 410, a data processing module 420, and a model training module 430, and a data optimizing module 440. One or more of the modules of the processing device 120 may be interconnected. The connection(s) may be wireless or wired. At least a portion of the processing device 120 may be implemented on a computing apparatus as illustrated in FIG. 2 or a mobile device as illustrated in FIG. 3.

The obtaining module 410 may obtain data and/or information. The obtaining module 410 may obtain data and/or information from the scanner 110, the storage device 130, the terminal(s) 140, or any devices or components capable of storing data via the network 150. In some embodiments, the obtaining module 410 may obtain a machine learning model and preliminary training data of at least one sample subject.

Exemplary machine learning models may include a neural network model (e.g., a deep learning model), a deep belief network (DBN), a stacked auto-encoders (SAE), a logistic regression (LR) model, a support vector machine (SVM) model, a decision tree model, a naive Bayesian model, a random forest model, or a restricted Boltzmann machine (RBM), a gradient boosting decision tree (GBDT) model, a LambdaMART model, an adaptive boosting model, a hidden Markov model, a perceptron neural network model, a Hopfield network model, or the like, or any combination thereof. Exemplary deep learning models may include a deep neural network (DNN) model, a convolutional neural network (CNN) model, a recurrent neural network (RNN) model, a feature pyramid network (FPN) model, etc. Exemplary CNN models may include a V-Net model, a U-Net model, a FB-Net model, a Link-Net model, or the like, or any combination thereof.

In some embodiments, the preliminary training data of the at least one sample subject may include raw data, listmode data, sinogram data, and/or image data of the at least one sample subject acquired by scanning the at least one sample subject using one or more first scanners. The machine learning model may be trained using training data that includes the preliminary training data of the at least one sample subject.

The data processing module 420 may process the preliminary training data. The processed preliminary training data may be determined as training input data. The data processing module 420 may process the preliminary training data by performing one or more data/image processing operations. The one or more data/image processing operations may be performed such that the preliminary training data may be superior to the generated training input data with respect to a data quality parameter. The data quality parameter refers to a parameter according to which the quality of data and/or images is evaluated. Merely by way of example, the data quality parameter may include at least one of a signal-to-noise ratio (SNR), a spatial resolution, an image contrast, etc. In some embodiments, the one or more data/image processing operations may include a data splitting operation, a data rebinning operation, or a downsampling operation, etc.

The model training module 430 may train a machine learning model. The model training module 430 may determine a trained machine learning model by training the machine learning model based on the training data. The training data may include the training input data generated by the data processing module 420 and the preliminary training data obtained by the obtaining module 410.

The data optimizing module 440 may optimize scanning data of a subject acquired by scanning the subject. The data optimizing module 440 may generate optimized scanning data of the subject by inputting the scanning data into a trained machine learning model. In some embodiments, the processing device 120 may further reconstruct one or more images based on the optimized second scanning data. The one or more reconstructed images may be transmitted to the terminal 140 and displayed on an interface (e.g., a screen) of the terminal 140.

It should be noted that the above descriptions of the processing device 120 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, the processing device 120 may include one or more other modules. In some embodiments, two or more units in the processing device 120 may form one module. However, those variations and modifications also fall within the scope of the present disclosure.

Figure 5:
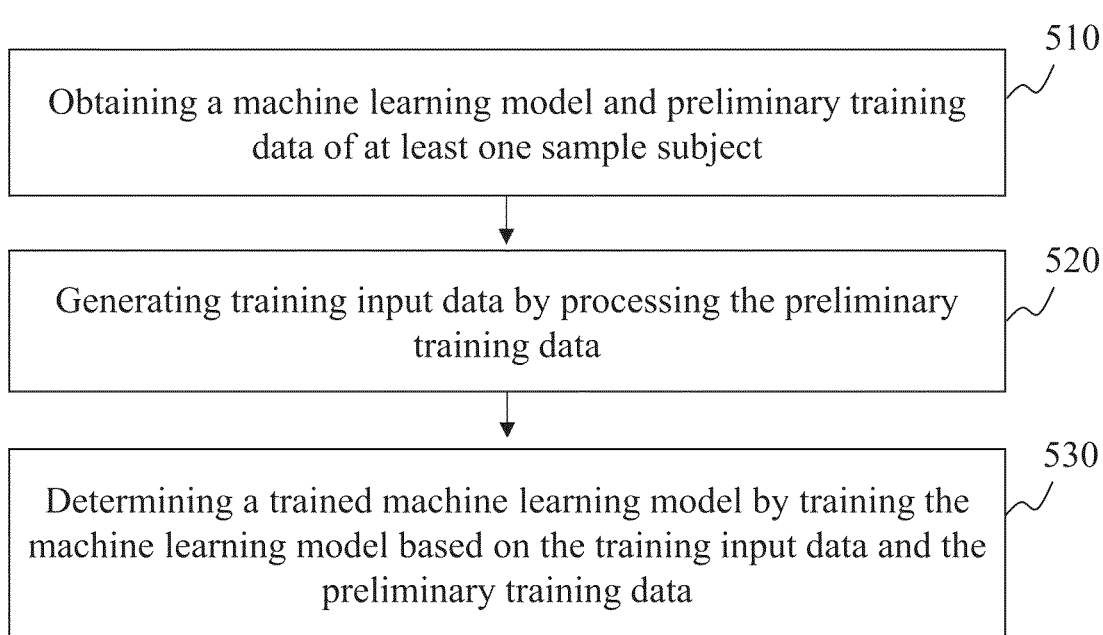
FIG. 5 includes a flowchart illustrating an exemplary process for determining a trained machine learning model according to some embodiments of the present disclosure.

FIG. 5 includes a flowchart illustrating an exemplary process for determining a trained machine learning model according to some embodiments of the present disclosure. In some embodiments, at least a portion of the process 500 may be performed by the processing device 120 (e.g., implemented in the computing device 200 shown in FIG. 2, the processing device illustrated in FIG. 4). In some embodiments, at least a portion of the process 500 may be performed by a terminal device (e.g., the mobile device 300 shown in FIG. 3) embodying software and/or hardware.

In 510, the processing device 120 (e.g., the obtaining module 410 or the processor 210) may obtain a machine learning model and preliminary training data of at least one sample subject.

The machine learning model may be a model to be trained. In some embodiments, the machine learning model may be retrieved from a storage device (e.g., the storage device 130, the storage 220, the storage 390, etc.). In some embodiments, the machine learning model may be obtained from an external device (e.g., a cloud server) relative to the imaging system 100.

Exemplary machine learning models may include a neural network model (e.g., a deep learning model), a deep belief network (DBN), a stacked auto-encoders (SAE), a logistic regression (LR) model, a support vector machine (SVM) model, a decision tree model, a naive Bayesian model, a random forest model, or a restricted Boltzmann machine (RBM), a gradient boosting decision tree (GBDT) model, a LambdaMART model, an adaptive boosting model, a hidden Markov model, a perceptron neural network model, a Hopfield network model, or the like, or any combination thereof. Exemplary deep learning models may include a deep neural network (DNN) model, a convolutional neural network (CNN) model, a recurrent neural network (RNN) model, a feature pyramid network (FPN) model, etc. Exemplary CNN models may include a V-Net model, a U-Net model, a FB-Net model, a Link-Net model, or the like, or any combination thereof.

Merely by way of example, the machine learning model may be a neural network model composed of two networks. The two networks may include a denoising network and an enhancement network. The denoising network may reduce noise in data or images. The enhancement network may facilitate an enhancement (e.g., a grey scale enhancement, a frequency domain enhancement, a color enhancement, etc.)

on data or images. Merely by way of example, the denoising network may be a CNN (also referred to as CNN-DE), and the enhancement network may be a CNN (also referred to as CNN-EN).

The at least one sample subject may be biological or non-biological. For example, the at least one sample subject may include one or more patients, one or more man-made objects, etc. As another example, the at least one sample subject may include at least one specific portion, organ, tissue, and/or physical point of the one or more patients. Merely by way of example, the at least one sample subject may include the head, the brain, the neck, the body, shoulders, arms, the thorax, the cardiac, the stomach, blood vessels, soft tissue, knees, feet, or the like, or a combination thereof, of the one or more patient.

In some embodiments, the preliminary training data of the at least one sample subject may include raw data, listmode data, sinogram data, and/or image data of the at least one sample subject. In some embodiments, the raw data, the listmode data, and/or the sinogram data may also be referred to as scanning data of the at least one sample subject. The preliminary training data of the at least one sample subject may be obtained from one or more first PET scanners (also referred to first scanners), a processing device (e.g., the processing device 120, the computing device 200, the mobile device 300), a storage device (e.g., the storage device 130, the storage 220, the storage 390, etc.), etc.

The raw data of the at least one sample subject may be generated by scanning the at least one sample subject using the one or more first scanners. When the one or more first scanners scan the at least one sample subject, detectors of the one or more first scanners may detect coincidence events in the form of, e.g., gamma phantoms. Electric signals may be generated in response to the detected coincidence events through a photoelectric conversion. The one or more first scanners may process the electric signals, and generate raw data of the at least one sample subject.

In some embodiments, the raw data of the at least one sample subject may be stored in the form of listmode data or sinogram data. The listmode data refers to raw data stored in the form of a table including a plurality of rows. Each of the plurality of rows may include information of a coincidence event, such as the time of the coincidence event occurs, energy values of two gamma photons produced by the coincidence event, time of fight (TOF) information of the two gamma photons, detector units that detect the the two gamma photons, coordinates of the detector units, etc. The sinogram data refers to raw data stored in the form of a sinogram. A coincidence event may be stored in the sinogram according to an angle of an LOR of two detector units that detect two gamma photons produced by the coincidence event and radial distances between the two detector units and a position of the coincidence event occurs.

The image data of the at least one sample subject refers to one or more images or data (e.g., pixel/voxel values and position information of corresponding pixels/voxels) reconstructed based on the raw data of the at least one sample subject according to an image reconstruction algorithm. Exemplary image reconstruction algorithms may include an expectation maximum (EM) algorithm, an ordered subset expectation maximization (OSEM) algorithm, a filtered back projection (FBP) algorithm, an iterative reconstruction algorithm (e.g., a statistical reconstruction algorithm), or the like, or any combination thereof. In some embodiments, during the image reconstruction process, an image enhancement operation (e.g., a TOF technique, a point spread function (PSF) technique, or the like, or a combination thereof) and/or a data/image correction operation (e.g., a image registration, an attenuation correction, a scattering correction, a detector efficiency normalization correction, a random correction, a decay correction, or the like, or a combination thereof) may be performed.

The machine learning model may be trained using training data that includes the preliminary training data of the at least one sample subject. The machine learning model may be a supervised learning model (e.g., a deep neural network model). The supervised learning model may be a model trained based on training data including training input data and training target data. The training input data refers to data input into the machine learning model (or a partially trained machine learning model) during the training process. The training target data refers to a target or reference of the output of the machine learning model (or a partially trained machine learning model) after corresponding training input data is input into the machine learning model (or a partially trained machine learning model) during the training process. The preliminary training data may be configured as training target data of the machine learning model.

In 520, the processing device 120 (e.g., the data processing module 420 or the processor 210) may generate training input data by processing the preliminary training data.

The generated training input data, which is generated by processing the preliminary training data, may also be referred to as processed training data. The preliminary training data may be processed by performing one or more data/image processing operations. The one or more data/image processing operations may be performed such that the preliminary training data may be superior to the generated training input data with respect to a data quality parameter. The data quality parameter refers to a parameter according to which the quality of data and/or images is evaluated. Merely by way of example, the data quality parameter may include at least one of a signal-to-noise ratio (SNR), a spatial resolution, an image contrast, etc.

In some embodiments, the one or more data/image processing operations may include a data splitting operation, a data rebinning operation, or a down-sampling operation, etc. The data splitting operation with respect to the preliminary training data may be an operation that splits a portion of data from the preliminary training data. In some embodiments, the portion of data may be split from the preliminary training data according to a scanning time period corresponding to the portion of data. For example, a portion of data that corresponds to a scanning time period of 1 minute (e.g., a first minute, a second minute, a third minute, etc.) may be split from preliminary training data acquired from a scan that lasts for a scanning time period of 5 minutes. The data rebinning operation may be an operation that re-organize the preliminary training data (e.g., the listmode data) such that at least a portion of the listmode data may be merged or split. In some embodiments, the preliminary training data may be rebinned in one or more dimensions. The one or more dimensions may include a size of a detector unit, TOF information, etc. The down-sampling operation may be an operation that re-samples and sparsify the preliminary training data. In some embodiments, the down-sampling operation may include a uniform down-sampling, a random down-sampling, etc. The uniform down-sampling refers to a down-sampling process in which the preliminary training data is re-sampled uniformly (e.g., at a regular interval). For example, as for listmode data, coincidence events in the listmode data may be re-sampled at a regular interval by performing a uniform down-sampling operation. The random down-sampling refers to a down-sampling process in which the preliminary training data is re-sampled randomly.

In some embodiments, the preliminary training data may include scanning data (also referred to as first scanning data) generated by a first PET scanner having an axial length exceeding a threshold axial length. The first PET scanner may include a plurality of detector rings arranged along an axial direction (e.g., the z-axis of the coordinate system 101 as illustrated in FIG. 1) of the first PET scanner. The axial length of the first PET scanner refers to a total length of the plurality of detetor rings of the PET scanner along the axial direction of the first PET scanner. The threshold axial length may be determined by a user, according to default settings of the imaging system 100, etc. Merely by way of example, the threshold axial length may be, for example, 1 meter, 1.1 meters, 1.2 meters, 1.3 meters, 1.4 meters, 1.5 meters, 1.6 meters, 1.8 meters, 2 meters, etc. In some embodiments, the first PET scanner having the axial length exceeding the threshold axial length may also be referred to as long-axis PET scanner. A PET scanner having the axial length being below the threshold axial length may also be referred to as short-axis PET scanner. For instance, a long-axis PET scanner may have an axial length of 1.94 meters, and a short-axis PET scanner may have an axial length of 0.48 meters.

In some embodiments, a long-axis PET scanner may be an extension of a structure of a short-axis PET scanner in the axial direction. A smallest unit of the extension may be, for example, a detector ring, a short-axis PET scanner, etc. Merely for illustration, a short-axis PET scanner may have four detector rings. The four detector rings may have a same length (e.g., 15 centimeters, 20 centimeters, 25 centimeters, 30 centimeters, etc.) in the axial direction. A long-axis PET scanner having eight detector rings may be an extension of the structure of the short-axis PET scanner. A smallest unit of the extension may be the short-axis PET scanner having four detector rings. In other words, the long-axis PET scanner may be a combination of two short-axis PET scanners. The formed long-axis PET scanner may be configured to process cross-coincidence data between different detector rings.

A main difference between the long-axis PET scanner and the short-axis PET scanner may be that the long-axis PET scanner has a higher sensitivity since the long-axis PET scanner acquires more data than the short-axis PET scanner during a same scanning time period (also referred to as acquisition time or acquisition time period). Differences with respect to other parameters, such as a spatial resolution, a TOF resolution, a quantitative accuracy between the long-axis PET scanner and the short-axis PET scanner, between the long-axis PET scanner and the short-axis PET scanner may be relatively small.

A theoretical value of a sensitivity of the long-axis scanner having an axial length of M may be increased by $(M/N)^2$ times relative to a theoretical value of a sensitivity of a short-axis scanner having an axial length of N, and a theoretical value of an SNR of scanning data generated by the long-axis PET scanner is increased by (M/N) times relative to a theoretical value of an SNR of the short-axis scanner. In fact, an actual value of the sensitivity and an actual value of the SNR of the long-axis scanner may be smaller than the theoretical value of the sensitivity and the theoretical value of the SNR of the long-axis scanner, respectively, due to random events and/or scatter events in the detected coincidence events. The random events and/or scatter events may reduce data quality. In some embodiments, an acceptance angle of coincidence counts of the long-axis scanner may be limited to reduce the random events and/or scatter events so as to improve the data quality.

The time that the short-axis PET scanner having the axial length of N takes to scan the whole body of a patient may be K times the time that the long-axis PET scanner having the axial length of M takes to scan the whole body of the patient, where $K \in [M/N, 2M/N-1]$. The lower limit M/N may correspond to a situation where there is no overlap between any two neighboring bed positions during the scanning process of the whole body of the patient using the short-axis PET scanner. The upper limit 2M/N−1 may correspond to a situation where there is a 50% overlap between two neighboring bed positions during the scanning process using the short-axis PET scanner.

It can be inferred that a scan performed using the long-axis PET scanner with a scanning time period of A/K minutes may be used to simulate a scan using the short-axis PET scanner with a scanning time period of A minutes. As for the training of the machine learning model, scanning data (e.g., the first scanning data) generated by a scan using the long-axis PET scanner with a scanning time period of A minutes may be used as the preliminary training data (or referred to as training target data), and scanning data generated by a scan using the long-axis PET scanner with a scanning time period of A/K minutes may be used as the training input data. The training input data (i.e., the scanning data generated by a scan using the long-axis PET scanner with a scanning time period of A/K minutes) may be substantially equivalent to or mimic scanning data generated by a scan using the short-axis PET scanner with a scanning time period of A minutes. In this case, the training target data may be obtained without prolonging a scanning time period of the at least one sample subject or increasing the dosage of the radiotracer intaken by the at least one sample subject. As used herein, substantially, when used to describe or qualify a feature (e.g., equivalent to), indicates that the deviation from the feature is below a threshold, e.g., 30%, 25%, 20%, 15%, 10%, 5%, etc.

In some embodiments, to generate the training input data, the processing device 120 may perform a down-sampling operation on the first scanning data generated by the first PET scanner at a preset down-sampling rate. The preset down-sampling rate may be determined by a user, according to default settings of the imaging system 100, etc. For instance, the preset down-sampling rate may be 1%, 2%, 3%, 5%, 10%, 15%, 20%, 25%, 30%, 35%, 40%, 45%, 50%, 55%, 60%, 65%, 70%, etc. The down-sampling operation may be uniform down-sampling or random down-sampling. In some embodiments, the down-sampled first scanning data may be designated as the training input data. In some embodiments, one or more images reconstructed based on the down-sampled first scanning data may be designated as the training input data. Since the training input data (e.g., the down-sampled first scanning data) is equivalent to scanning data generated by a short-axis PET scanner, the training target data (e.g., the first scanning data) may be superior to the training input data with respect to the SNR.

In some embodiments, the preliminary training data may include scanning data generated by a first PET scanner having a TOF resolution exceeding a threshold TOF resolution. The higher the TOF resolution is, the higher a positioning accuracy of a photon pair of a coincidence event may be. Thus, errors caused by scattering, a depth of interaction, etc., may be reduced. In some embodiments, the scanning data may be listmode data (also referred to as first listmode data). The first listmode data may be in the form of a matrix, a vector, etc. For example, the first listmode data may be represented by (Ia, Ib, Ra, Rb, Ta, Tb). The parameters a and b represent detector units of a first scanner that are connected by an LOR of a coincidence event in the first listmode data, in which the first scanner include an array of detector units. Ia denotes a serial number of the detector unit a along a circumferential direction of a detector ring of the first scanner, Ib denotes a serial number of the detector unit b along the circumferential direction, Ra denotes a serial number of the detector unit a along an axial direction of the detector ring of the first scanner, Rb denotes a serial number of the detector unit b along the axial direction of the detector ring of the first scanner, Ta denotes TOF timestamp information recorded by the detector unit a, and Tb denotes TOF timestamp information recorded by the detector unit b. The TOF timestamp information may be represented by Tbin. Tbin may be a smallest unit of the TOF information of the first listmode data. Assuming that a window width of a coincidence window for recording coincidence events is W nanoseconds (ns) and that count of timestamps for recording the TOF may be N, a window width of each timestamp may be W/N ns.

The threshold TOF resolution may be determined by a user, according to default settings of the imaging system 100, etc. Merely by way of example, the threshold TOF resolution may be, for example, 300 picoseconds, 250 picoseconds, 200 picoseconds, 150 picoseconds, etc. In some embodiments, the first PET scanner having the TOF resolution exceeding the threshold TOF resolution may also be referred to as a high TOF resolution PET scanner. A PET scanner having the TOF resolution that is below the threshold TOF resolution may also be referred to as a low TOF resolution PET scanner. For instance, a TOF resolution of a high TOF resolution PET scanner may be 190 picoseconds, and a TOF resolution of a low TOF resolution PET scanner may be 400-500 picoseconds. Assuming that all other parameters of the first PET scanner remain the same, the higher the TOF resolution is, the smaller the window width of a timestamp may be, the higher the total count of the timestamps may be, and the higher an image contrast may be, which in turn may make it easier to detect a lesion of a small size.

In some embodiments, the processing device 120 may perform a rebinning operation on the first listmode data according to, e.g., preset TOF information. The preset TOF information may be determined by a user, according to default settings of the imaging system 100, etc. Merely for illustration, TOF information of the first listmode data may be X Tbin. X may be an integer, e.g., 10, 20, 40, etc. A TOF resolution corresponding to the TOF information of X Tbin may exceed the threshold TOF resolution. A TOF resolution corresponding to the preset TOF information may be below the threshold TOF resolution.

In some embodiments, the TOF information of the first listmode data may be rebinned according to the Equations (1)-(3):

$$N_L = \frac{g_{FWHM}^H}{g_{FWHM}^L} N_H, \tag{1}$$

$$T_a^L = \left\lfloor \frac{N_L}{N_H} T_a^H \right\rfloor, \tag{2}$$

$$T_b^L = \left\lfloor \frac{N_L}{N_H} T_b^H \right\rfloor, \tag{3}$$

where $$g_{FWHM}^{H} \text{ and } g_{FWHM}^{L}$$

denote the TOF resolution (i.e., a full width at half maximum (FWHM) of a kernel function) of the high TOF resolution PET scanner and the TOF resolution of the low TOF resolution PET scanner, respectively, $N_H$ and $N_L$ denote total counts of the timestamps of the high TOF resolution PET scanner and the low TOF resolution PET scanner, respectively, $$T_a^{H} \text{ and } T_a^{L}$$

denote serial numbers of the timestamps of the detector unit a of the high TOF resolution PET scanner and the TOF resolution of the low TOF resolution PET scanner, respectively, $$T_b^{H} \text{ and } T_b^{L}$$

denote serial numbers of the timestamps of the detector unit b of the high TOF resolution PET scanner and the TOF resolution of the low TOF resolution PET scanner, respectively, and the symbol $\lfloor \; \rfloor$ represents a maximum integer that is smaller than or equal to the value in the symbol since a serial number of a timestamp is an integer.

For instance, the TOF resolution corresponding to the preset TOF information may be 400 picoseconds (e.g., recorded by 40 timestamps), and the TOF resolution corresponding to the TOF information of the first listmode data may be 200 picoseconds (e.g., recorded by 20 timestamps). In this case, a pair of consecutive Tbins may be combined into a new Tbin. The preset TOF information may be represented by X/2 Tbin. The first listmode data may be rebinned according to the preset TOF information. In some embodiments, the rebinned first listmode data may be designated as the training input data. In some embodiments, one or more images reconstructed based on the rebinned first listmode data may be designated as the training input data. Similarly, the training input data (e.g., the rebinned first listmode data) may be substantially equivalent to or mimic scanning data generated by a low TOF resolution PET scanner, and the training target data (e.g., the first listmode data) may be superior to the training input data with respect to the image contrast.

In some embodiments, the preliminary training data may include scanning data generated by a first PET scanner having a detector unit size being below a threshold detector unit size. In some embodiments, the scanning data may be listmode data (also referred to as second listmode data). The first PET scanner may include one or more detector rings. Each of the one or more of detector rings may include a plurality of detector units. In some embodiments, the second listmode data may be in the form of a matrix, a vector, etc. For example, the second listmode data may be represented by (Ia, Ib, Ra, Rb).

In some embodiments, the plurality of detector units may have a same size. The size may also be referred to as detector unit size. The threshold detector unit size may be determined by a user, according to default settings of the imaging system 100, etc. Merely by way of example, the threshold detector unit size may be, for example, 2.8 millimeters (mm)×2.8 mm, 3.0 mm×3.0 mm, 3.2 mm×3.2 mm, 3.5 mm×3.5 mm, etc. In some embodiments, the first PET scanner having the detector unit size being below the threshold detector unit size may also be referred to as a small detector-unit-size PET scanner. A PET scanner having the detector unit size exceeding the threshold detector unit size may also be referred to as a large detector-unit-size PET scanner. For instance, a detector unit size of a small detector-unit-size PET scanner may be 2.7 mm×2.7 mm, and a detector unit size of a large detector-unit-size PET scanner may be 4 mm×4 mm. The smaller the detector unit size is, the higher a spatial resolution of the scanning data may be.

In some embodiments, the processing device 120 may determine coordinates of virtual detector units based on coordinates of detector units of the first PET scanner (e.g., the small detector-unit-size PET scanner) and a preset detector unit size. Virtual detector units may be determined by re-grouping the detector units based on the preset detector unit size. For instance, the first PET scanner may include 112 detector rings, and each detector ring may include 1024 detector units. After re-grouping the detector units based on the preset detector unit size, a virtual PET scanner may include 32 virtual detector rings, and each virtual detector ring may include 256 virtual detector units; that is, grouping more than one detector unis to form a virtual detector unit. The coordinates of detector units of the first PET scanner may include coordinates of a center and/or an edge of the detector unit along the axial direction (e.g., the z-axis of the coordinate system 101 as illustrated in FIG. 1). A detector unit size of the first PET scanner may be below the threshold detector unit size. The preset detector unit size may be determined by a user, according to default settings of the imaging system 100, etc. The preset detector unit size may exceed the threshold detector unit size. The preset detector unit size may be larger than the detector unit size of the first PET scanner. The coordinates of virtual detector units may include coordinates of a center and/or an edge of the virtual detector unit along the axial direction. The coordinates of the virtual detector units may be determined by re-organizing the coordinates of detector units of the first PET scanner according to the preset detector unit size.

Merely by way of example, assuming that the detector unit sizes of the large detector-unit-size PET scanner and the small detector-unit-size PET scanner may be $d^L$ mm×$d^L$ mm and $d^H$ mm×$d^H$ mm, respectively, for a same detector unit, coordinates of the detector unit in the large detector-unit-size PET scanner and the small detector-unit-size PET scanner may be ($I^H$,$R^H$) and ($I^L$,$R^L$), respectively. A maximum value of $I^L$ ($I^H$) may correspond to a count of detector units of each detector ring along the axial direction. A maximum value of $R^L$ ($R^H$) may correspond to a count of the detector rings along the axial direction. A conversion relationship between the coordinates of a detector unit in the large detector-unit-size PET scanner and a corresponding detector unit in the small detector-unit-size PET scanner may be provided in Equations (4)-(5):

$$I^L = \left\lfloor \frac{d_H}{d_L} I^H \right\rfloor, \tag{4}$$

and $$R^L = \left\lfloor \frac{d_H}{d_L} R^H \right\rfloor. \tag{5}$$

As used herein, a first detector unit in the large detector-unit-size PET scanner and a second detector unit in the small detector-unit-size PET scanner are considered corresponding to each other. After the coordinates of the virtual detector units are determined, the processing device 120 may perform a rebinning operation on the second listmode data according to the determined coordinates of the virtual detector units. In some embodiments, the rebinning operation on the second listmode data according to the determined coordinates of the virtual detector units may be performed in a similar way as the rebinning operation performed on the first listmode data as two or more rows of the second listmode data may be merged into one row of the second listmode data. In some embodiments, the rebinned second listmode data may be designated as the training input data. In some embodiments, one or more images reconstructed based on the rebinned second listmode data may be designated as the training input data. The training input data (e.g., the rebinned second listmode data) may be substantially equivalent to or mimic scanning data generated by a large detector-unit-size PET scanner, and the training target data (e.g., the second listmode data) may be superior to the training input data with respect to the spatial resolution.

In some embodiments, the preliminary training data may include scanning data generated by a first PET scanner having a noise equivalent count rate (NECR) exceeding a threshold NECR. The NECR may be a parameter representing the data quality of the scanning data. In some embodiments, the scanning data may be listmode data (also referred to as third listmode data). The NECR may be determined according to Equation (6)

$$NECR = \frac{T^2}{P}, \tag{6}$$

where T denotes a count rate of true coincidence events, and P denotes a total count rate. The total count rate P may equal a sum of the count rate of the true coincidence events, a count rate of scattered coincidence events, and a count rate of random coincidence events. The higher the NECR is, the higher the data quality of the scanning data (e.g., the third listmode data) may be.

The threshold NECR may be determined by a user, according to default settings of the imaging system 100, etc. A first PET scanner having the NECR above the threshold NECR may also be referred to as a high NECR PET scanner. A first PET scanner having the NECR below the threshold NECR may also be referred to as a low NECR PET scanner.

The third listmode data may be stored in the form of a table including a plurality of rows. Each of the plurality of rows may include data of a coincidence event. The information of a coincidence event may include a coincidence mark for identifying whether the data belongs to a prompt coincidence count (marked as prompt) or a delayed coincidence count (marked as delay). As used herein, the delayed coincidence count refers to a count of delayed coincidence events recorded in the delayed window. The delayed window may have a same window width as the coincidence window. A time interval between the delayed window and the prompt coincidence window may be relatively large so that all the data recorded in the delayed window may be random coincidence count(s). The delayed coincidence count(s) may be used to evaluate a count of the random coincidence event(s). In some embodiments, a count of the prompt coincidence count and a count of the delayed coincidence count may be obtained. The count of the delayed coincidence count may be denoted by D. The count of the prompt coincidence count may be denoted by p.

In some embodiments, a data set may be extracted from the delayed coincidence counts. For instance, the data set may be extracted randomly from the delayed coincidence counts. As another example, the data set may include multiple continuous counts in the delayed coincidence counts. The data set may be determined according to Equation (7):

$$k = \frac{p}{y} - p, \tag{7}$$

where k denotes a number or count of delayed coincidence events recorded in the data set, y denotes a ratio of the NECR of a low NECR PET scanner to the NECR of a high NECR PET scanner, and $y \in (0,1)$.

In some embodiments, two data sets may be generated by duplicating the data set and then modify the two duplicated data sets. For instance, coincidence marks of one data set may remain unchanged, and coincidence marks of the other data set may be replaced with p. The fourth listmode data may be generated by incorporating the two data sets into the third listmode data. The fourth listmode data may be designated as the training input data. In some embodiments, one or more images reconstructed based on the fourth listmode data may be designated as the training input data. The training input data (e.g., the fourth listmode data) may be substantially equivalent to or mimic scanning data generated by a low NECR PET scanner, and the training target data (e.g., the third listmode data) may be superior to the training input data with respect to the SNR.

In some embodiments, preliminary training data acquired in one scan of a sample subject may be used to generate multiple sets of training input data. For instance, the one or more operations (e.g., the data splitting operation, the data rebinning operation, and/or the down-sampling operation) may be performed to process the same preliminary training data, respectively, so as to generate the multiple sets of training input data. Accordingly, multiple pairs of training samples may include (or referred to as share) same preliminary training data. The multiple pairs of training samples may be used to train the machine learning model.

In 530, the processing device 120 (e.g., the model training module 430 or the processor 210) may determine a trained machine learning model by training the machine learning model based on the training input data and the preliminary training data.

In some embodiments, the machine learning model may be a supervised learning model. Training input data (e.g., the training input data generated in 520) and corresponding training target data (e.g., the preliminary training data) may be input into the machine learning model. The trained machine learning model may be trained based on the input training input data and the corresponding training target data.

In some embodiments, the training data including the training input data and the training target data may be in the form of training images. Merely by way of example, the training images may be images having sizes of 249×249× 671 with a voxel size of 2.4×2.4×2.68 mm³ and 499×499× 1342 with a voxel size of 1.2×1.2×1.34 mm³ for two different networks (e.g., the CNN-DE and CNN-EN) having different sizes (e.g., 2.4 millimeters and 1.2 millimeters), respectively.

In some embodiments, the training data may further be processed by performing a training data processing operation. The training data processing operation may include, for example, an augmentation operation (e.g., flipping, rotating, etc.), a normalization operation (e.g., a z-core normalization), a correction operation (e.g., a scattering correction, a normalization correction, a dead time correction, an attenuation correction, a random correction, a decay correction, etc.).

Before the training process starts, the processing device 120 may initialize value(s) of one or more model parameters of the machine learning model. The training process of the machine learning model may include one or more iterations for iteratively updating the value(s) of the one or more model parameters of the machine learning model based on the training data until a termination condition is satisfied in a certain iteration. Exemplary termination conditions may include that a value of a loss function obtained in the certain iteration is less than a threshold value, that a preset count of iterations have been performed, that the loss function converges such that the difference of the values of the loss function obtained in a previous iteration and the current iteration is within a threshold value, etc. The loss function may be used to measure a discrepancy between an output of the (partially) machine learning model in an iteration and the corresponding training target data. Exemplary loss functions may include a focal loss function, a log loss function, a cross-entropy loss, a Dice ratio, or the like. After the training process is terminated, the trained machine learning models may be determined.

Descriptions below is an example of image denoising for a PET image, which is merely for illustration purposes. According to the example, a deep learning model may be provided for reducing noise and improving a SNR of a PET image. The deep learning model may be, for example, a U-net. Training data of the deep learning model may include scanning data of multiple (e.g., 80, 100, 200, etc.) sample subjects acquired by scanning the multiple sample subjects using a long-axis PET scanner. Merely by way of example, the long-axis PET scanner may be composed of eight PET detector rings. Each of the eight PET detector rings, which can be used as a short-axis PET scanner, may have an axial field of view (FOV) of 24 centimeters. The long-axis PET scanner may have an axial FOV of 194 centimeters. A sensitivity of the long-axis PET scanner may be about 40 times a sensitivity of a short-axis PET scanner. Under a same scanning time and a same radiotracer dosage, a SNR of the long-axis PET scanner may be more than 6 times a SNR of the short-axis PET scanner. The long-axis PET scanner may cover an entire sample subject in a single scan. For the same sample subject, a short-axis PET scanner may need to perform multiple scans on different portions of the sample subject. A scanning time of the long-axis PET scanner on the sample subject may be, for example, 1 minute, while a scanning time of the short-axis PET scanner on the same sample subject (for a same radiotracer dosage) may be, for example, 5 minutes, to achieve similar image quality.

During a scanning process of each of the multiple sample subjects using the long-axis PET scanner, the sample subject may be injected with a PET tracer (or referred to as a radiotracer including, e.g., F18-Fluorodeoxyglucose (FDG)) at a preset injected dose (e.g., 0.1 millicurie per kilogram (mCi/kg)). The sample subject may be scanned, and scanning data of the sample subject may be generated. In some embodiments, the scanning data may be determined as preliminary training data of the sample subject. In some embodiments, one or more preliminary images reconstructured based on the scanning data may be determined as preliminary training data of the sample subject. The preliminary training data may be configured as the training target data of the deep learning model.

The preliminary training data (e.g., the scanning data or the one or more images) may be down-sampled at a preset down-sampling rate (e.g., 10%, 20%, etc.) uniformly or randomly. In some embodiments, the down-sampled preliminary training data may be designated as the training input data. In some embodiments, the one or more images reconstructed based on the down-sampled preliminary training data may be designated as the training input data. The down-sampled preliminary training data or the one or more images reconstructed based on the down-sampled preliminary training data may have a relatively low SNR, which may be close to scanning data acquired by a conventional short-axis PET scanner having an axial FOV of 20-30 centimeters, or images reconstructed based on the scanning data acquired by the conventional short-axis PET scanner. The training input data and the training target data may be input into the deep learning model so as to determine a trained deep learning model. The trained deep learning model may be configured to generate optimized scanning data (also referred to as optimized second scanning data) of a subject by inputting into the trained machine learning model scanning data (also referred to as second scanning data) that are acquired by scanning the subject using a scanner (also referred to as a second scanner). The second scanner may be different from at least one of the one or more first scanners (e.g., the first PET scanners as described in 520, which vary in the axial length, the detector unit size, the T) that scans the at least one sample subject and generates the training data (e.g., the preliminary training data) for training the machine learning model. Details regarding the generation of the optimized scanning data can be found elsewhere in the present disclosure. See, for example, FIG. 6 and the descriptions thereof.

It should be noted that the above description is merely provided for the purposes of illustration, and not intended to limit the scope of the present disclosure. For persons having ordinary skill in the art, multiple variations and modifications may be made under the teachings of the present disclosure. However, those variations and modifications do not depart from the scope of the present disclosure. For example, as for the CNN-EH, PET images reconstructed with insufficient iterations (e.g., one third, a half, etc. of the preset count of the iterations) may be used as training input data of the CNN-EH, and PET images reconstructed with sufficient iterations (e.g., the preset count of the iterations) may be used as training target data of the CNN-EH. As another example, the machine learning model may have a certain degree of robustness. regardless of performance and/or structural differences between the long-axis PET scanner and the short-axis PET scanner, such as a time resolution, a radial FOV, a photoelectric conversion module, a cooling system, etc., a machine learning model trained according to the operations 510-530 can still be applied to the optimization of scanning data acquired by the short-axis PET scanner.

FIG. 6 includes a flowchart illustrating an exemplary process for generating optimized scanning data of a subject according to some embodiments of the present disclosure. In some embodiments, at least a portion of the process 600 may be performed by the processing device 120 (e.g., implemented in the computing device 200 shown in FIG. 2, the processing device illustrated in FIG. 4). In some embodiments, at least a portion of the process 600 may be performed by a terminal device (e.g., the mobile device 300 shown in FIG. 3) embodying software and/or hardware.

In 610, the processing device 120 (e.g., the model training module 430 or the processor 210) may obtain a trained machine learning model, wherein the trained machine learning model is trained using training data that includes preliminary training data acquired by scanning at least one sample subject using one or more first scanners. The trained machine learning model may be determined according to a method as described elsewhere in the disclosure. See, e.g., FIG. 5 and the description thereof, which are not repeated here.

In 620, the processing device 120 (e.g., the obtaining module 410 or the processor 210) may obtain scanning data of a subject acquired by scanning the subject using a second scanner that is different from at least one of the one or more first scanners.

The second scanner (e.g., the scanner 110) may perform a scan on, for example, a scanning region which includes the subject. The scan may be performed according to a scanning protocol. The scanning protocol may include one or more parameters of the second scanner, a size of the scanning region, position information of the scanning region, information regarding image contrast and/or ratio, or the like, or any combination thereof. After the scan is performed, scanning data of the subject may be generated. The scanning data acquired by scanning the subject using the second scanner may also be referred to as second scanning data.

The second scanner may be different from at least one of the one or more first scanners that scans the at least one sample subject and generates the training data (e.g., the preliminary training data) for training the machine learning model. For example, the second scanner may be a short-axis PET scanner. As another example, the second scanner may be a low TOF resolution PET scanner. As a further example, the second scanner may be a large detector-unit-size PET scanner.

In 630, the processing device 120 (e.g., the data optimizing module 440 or the processor 210) may generate optimized scanning data of the subject by inputting the scanning data into the trained machine learning model.

The optimized scanning data (also referred to as optimized second scanning data) of the subject may be generated by inputting into the trained machine learning model the second scanning data of the subject that is acquired by scanning the subject using the second scanner. In some embodiments, the processing device 120 may further reconstruct one or more images based on the optimized second scanning data. The one or more reconstructed images may be transmitted to the terminal 140 and displayed on an interface (e.g., a screen) of the terminal 140.

In some embodiments, the trained machine learning model may be associated with the PET tracer injected into the at least one sample subject. Exemplary PET tracers may include F18-FDG, F18-fluorodopa (FDOPA), C11-methionine (MET), etc. If a PET tracer injected into the subject is the same as the PET tracer injected into the at least one sample subject, the trained machine learning model may be used to generate the optimized second scanning data of the subject by inputting into the trained machine learning model the second scanning data. If a PET tracer injected into the subject is different from the PET tracer injected into the at least one sample subject, the trained machine learning model may not be used to generate the optimized second scanning data of the subject, and another trained machine learning model associated with the PET tracer injected into the subject may be determined according to the process 500. The optimized second scanning data of the subject may be generated by inputting the second scanning data into the another trained machine learning model. For example, in a case that a PET tracer injected into the at least one sample subject is F18-FDG, and the trained machine learning model is determined based on the training data acquired by scanning the at least one sample subject using the one or more first scanners, the trained machine learning model may be associated with the PET tracer of F18-FDG. If the PET tracer injected into the subject is F18-FDG, the trained machine learning model may be used to generate the optimized second scanning data of the subject. If the PET tracer injected into the subject is C11-MET, another trained machine learning model associated with the C11-MET may be determined according to the process 500. The optimized second scanning data of the subject may be generated by inputting the second scanning data into the other trained machine learning model.

Figure 7:
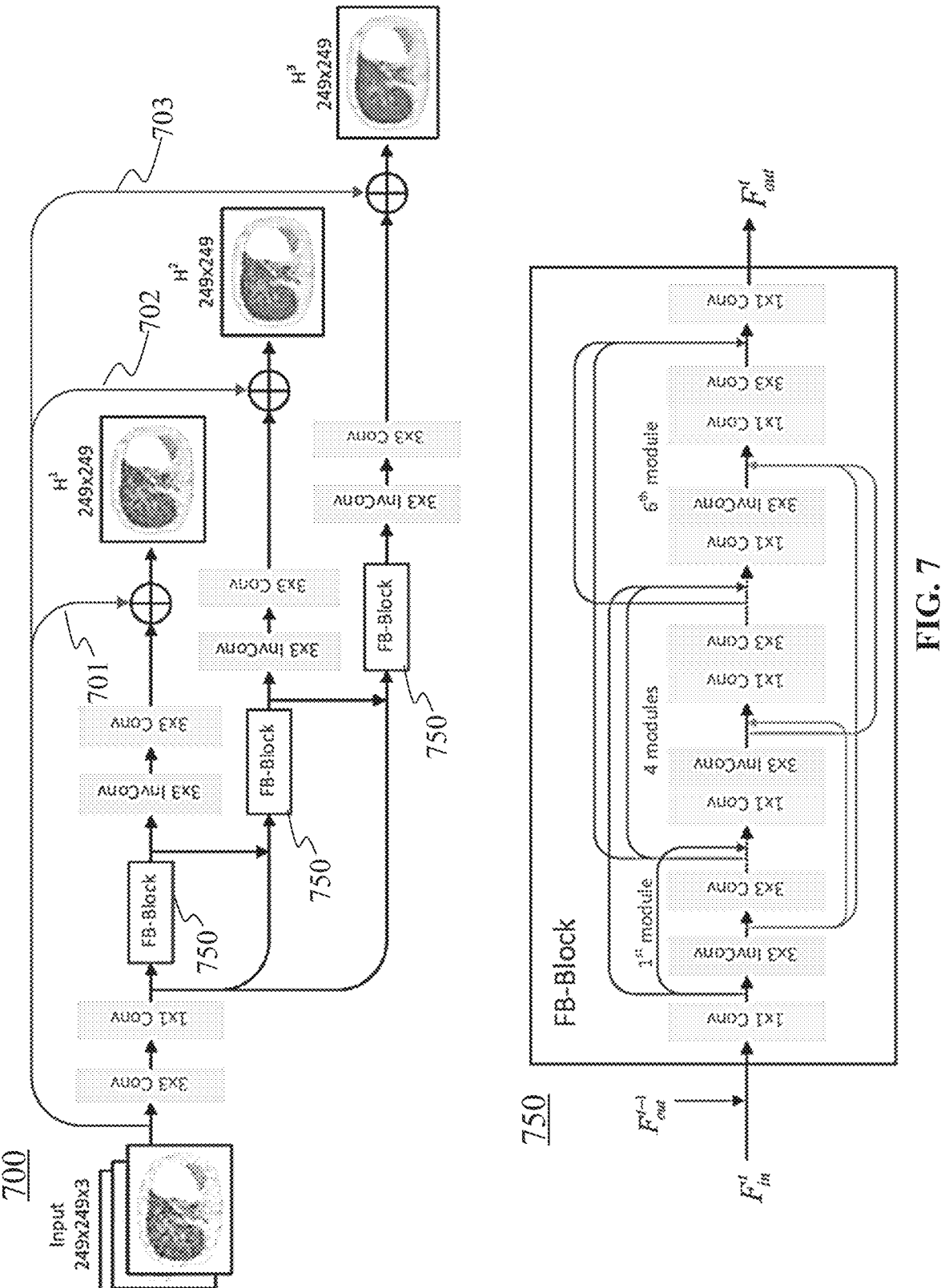
FIG. 7 is a schematic diagram of a network structure of CNN-DE and CNN-EH according to some embodiments of the present disclosure.

FIG. 7 is a schematic diagram of a network structure of CNN-DE and CNN-EH according to some embodiments of the present disclosure. As illustrated in FIG. 7, the network CNN-DE and CNN-EH (also referred to as network 700 for brevity) may have three branches. Each of the three branches may include a plurality of layers (e.g., 3×3 convolution layers, 1×1 convolution layers, 3×3 inverse convolution layers, etc.) and a feedback-block (FB-block) 750. H1, H2 and H3 may be outputs of the three branches, respectively. Solid lines 701-703 may represent residual connections between the input and the output of each of the three branches, respectively. The residual connections may establish shortcuts to jump over one or more layers of the network 700 so as to solve the problem of vanishing gradient and improve the efficiency of the training process of the network 700. The FB-block 750 may include a plurality of convolution layers and duplicate modules. The convolution layers may reduce a count of feature maps and accelerate an inference process of the the network 700. The duplicate modules may include paired inverse convolution layers and convolution layers. The FB-block 750 may enrich the expression of high-level features through dense connections in the FB-block 750. The dense connections may make the transmission of gradients and features more effective and reduce a count of parameters of the network 700. The dense connections may facilitate concatenation of features of different convolution layers.

The 3×3 convolution layers (also referred to as 3×3 Conv as shown in FIG. 7) refer to convolution layers having kernel sizes of 3×3 pixels. The 1×1 convolution layers (also referred to as 1×1 Conv as shown in FIG. 7) refer to convolution layers having kernel sizes of 1×1 pixel. The 3×3 convolution layers and 1×1 convolution layers may extract features of training input data. The 3×3 inverse convolution layers (also referred to as 3×3 InvConv as shown in FIG. 7) refer to inverse convolution layers having kernel sizes of 3×3 pixels.

$$F_{out}^{t-1}$$

represents a high-level feature after a (t−1)-th branch, which serves as feedback information to guide a low-level feature expression $$F_{in}^{t}$$

of a t-th-branch and enables a learning and expression capability of the network 700 to enhance gradually, and t may be 1, 2, or 3. Each of the three branches of the network 700 may share same weights, which may greatly compress a size of the network 700 and reduces an inference time of the network 700. The output of the last branch is the final output of the network 700.

Merely by way of example, a loss function (also referred to as objective function) of the network 700 may be determined according to Equation (8):

$$\text{Loss}(H^t, G) = \frac{1}{T}\sum_{t=1}^{T}\left|H^t - G\right|, \tag{8}$$

where $H^t$ denotes an output (e.g., an output image) of the t th-branch and G denotes training target data (e.g., a target image). T represents a count of the branches. As for the network 700, T may be set to 3. In some embodiments, a back propagation algorithm may be used to update parameters of the network 700 based on an adaptive moment estimation (ADAM) optimization algorithm and a cyclical learning rate. Minimum and maximum values for the cyclical learning rate may be, for example, $1{\times}e^{-5}$ and $1{\times}e^{-4}$, respectively. In some embodiments, the network settings (e.g., model parameters) are the same for both the CNN-DE and the CNN-EH.

FIGS. 8A-8C illustrate exemplary diagrams of contrast recoveries, background variations and contrast to noise ratios of images of an international electrotechnical commission (IEC) body phantom reconstructed based on simulated fast scan data and full data according to different approaches according to some embodiments of the present disclosure.

The different approaches may include an ordinary-poisson (OP)-OSEM with a Gaussian filtering (denoted as GF), an OP-OSEM with a U-Net (denoted as DLU), an OP-OSEM with an FB-Net (denoted as DLFB), and a deep progressive learning (e.g., involving the network 700, which is composed of the CNN-DE and the CNN-EH) (denoted as DPL). The networks of DLU, the DLFB, and the DPL may be trained according to the process 500 as illustrated in FIG. 5.

The IEC body phantom was used to evaluate the performance of the different approaches for body imaging. The IEC body phantom was scanned by a digital TOF PET/CT scanner, which has an axial length of 30 centimeters and a system sensitivity of 15 kcps/MBq.

The IEC body phantom was filled with F18-FDG of 48.8 MBq, and scanned for 5 minutes for assessing performance of the exemplified approaches in terms of bias and variance. A plurality of ROIs were defined in an image of the IEC body phantom. The plurality of ROIs included hot spheres (e.g., spheres having higher contrast ratios), cold spheres (e.g., spheres having lower contrast ratios), etc. A concentration ratio of a hot sphere to a background in an image of the IEC body phantom was set to 4:1. Scanning data (e.g., in the form of listmode data, which is also referred to as full data) of the IEC body phantom was down-sampled randomly at a down-sampling rate of 20% to simulate a fast PET scan, which has an equivalent scanning time of 60 seconds.

A full width at half maximum (FWHM) of the Gaussian filter was set to 4 mm. The DLU included a single neural network with the architecture of U-Net. The DLFB included a single neural network with the architecture of FB-Net. An image size was 249×249×113 with a voxel size of 4×2.4× 2.68 mm³ for the IEC body phantom. All the images of the IEC body phantom were reconstructed with TOF and resolution modeling, and corrected by performing an image correction operation (e.g., a scattering correction, a normalization correction, a dead time correction, an attenuation correction, a random correction, a decay correction, or the like, or a combination thereof).

A contrast recovery (CR) and a background variation (BV) for each of one or more ROIs of the IEC body phantom was determined according to Equations (9)-(11):

$$CR_{H,j} = \frac{C_{H,j}/C_{B,j} - 1}{A - 1} \times 100\%, \tag{9}$$

$$CR_{C,j} = \left(1 - C_{C,j}/C_{B,j}\right) \times 100\%, \tag{10}$$

and $$BV_j = \frac{\sqrt{\sum_{k=1}^{K}(C_{B,j,k} - C_{B,j})^2/(K-1)}}{c_{B,j}} \times 100\%, \tag{11}$$

where $C_{H,j}$ denotes an average counts of coincidence events in the ROI of a hot sphere j, $C_{C,j}$ denotes an average counts of coincidence events in the ROI of a cold sphere j, $C_{B,j}$ denotes an average counts of coincidence events in the ROI of a sphere j in the background, A denotes a concentration ratio of a standard hot sphere to the background, $BV_j$ denotes a background variability for the sphere j, and K denotes a count of selected background ROIs. K was set to 60.

A contrast to noise ratio (CNR) for each sphere of the IEC body phantom was determined according to Equations (12) and (13):

$$CNR_{H,j} = \frac{CR_{H,j}}{BV_j}, \tag{12}$$

and $$CNR_{C,j} = \frac{CR_{C,j}}{BV_j}. \tag{13}$$

As for the IEC body phantom, the performance of the exemplified approaches (i.e., the GF, the DLU, the DLFB, and the DPL) were compared using the simulated fast scan data (60 seconds) and the full data (300 seconds). As shown in FIGS. 8A-8C, the CR, BV, and CNR of images generated using the simulated fast scan data and the full data according to the DLU, the DLFB, and the DPL appear to be better than the CR, BV, and CNR of images generated according to the GF. Besides, the CR, BV, and CNR of images generated using the simulated fast scan data according to the DLU, the DLFB, and the DPL appear be close to the CR, BV, and CNR of images generated using the full data, respectively, among which the CR of the images generated using the simulated fast scan data according to the DLU, the DLFB, and the DPL are closest to the images generated using the full data. The DPL may have better performance on the CR, BV and CNR than the GF, the DLU, and the DLFB. The GF may have poorer performance on the CR, BV and CNR than the DLU, the DLFB, and the DPL.

FIG. 9 illustrates images of an IEC body phantom reconstructed using simulated fast scan data and full data according to different approaches according to some embodiments of the present disclosure. As shown in FIG. 9, regardless of whether the simulated fast scan data or the full data were used for image reconstruction, images reconstructed according to the DLU, the DLFB, and the DPL appear to have better image quality than images reconstructed according to the GF. In addition, the image quality of images reconstructed according to the DLU, the DLFB, and the DPL using the simulated fast scan data appears to be close to the image quality of images reconstructed according to the GF using the full data.

FIGS. 10A and 10B illustrate exemplary diagrams of radioactivity concentration ratios and contrast recoveries of images of a Hoffman brain phantom generated based on simulated fast scan data and full data according to different approaches according to some embodiments of the present disclosure.

The different approaches (e.g., the GF, the DLU, the DLFB, and the DPL) and settings (e.g., a network architecture, a reconstruction algorithm, an image correction operation, etc.) of networks of the different approaches may be the same as the approaches and corresponding settings exemplified above.

The Hoffman brain phantom was used to evaluate the performance of the different approaches for brain imaging. The Hoffman brain phantom was filled with F18-FDG of 41.8 MBq, and scanned for 30 minutes. The Hoffman brain phantom was scanned by a digital TOF PET/CT scanner, which has an axial length of 30 cm and a system sensitivity of 15 kcps/MBq. Scanning data (e.g., in the form of listmode data, which is also referred to as full data) of the Hoffman brain phantom was down-sampled to 1, 2, 3, 5 and 10 minutes to simulate typical clinical scans.

A radioactivity concentration ratio (RCR) and a contrast recovery ($CR_m$) of the Hoffman brain phantom may be determined according to Equations (14) and (15):

$$RCR = \frac{C_{GM}}{C_{WM}}, \qquad (14)$$

and $$CR_m = \frac{C_{GM} - C_{CSF}}{C_{GM}} \times 100\%, \qquad (15)$$

where $C_{GM}$, $C_{WM}$, and $C_{CSF}$ represent average counts of coincidence events in ROIs in the gray matter (GM), the white matter (WM), and the cerebrospinal fluid (CSF), respectively, in the Hoffman brain phantom.

As shown in FIG. 10A, RCRs of images reconstructed, based on scanning data corresponding to different scanning time periods, according to the DLU, the DLFB, and the DPL appear to be better than RCRs of images reconstructed according to the GF. The DPL has better performance on the RCR than the GF, the DLU, and the DLFB. The GF has poorer performance on the RCR than the DLU, the DLFB, and the DPL. Similarly, as shown in FIG. 10B, $CR_m$s of images reconstructed, based on scanning data corresponding to different scanning time periods, according to the DLU, the DLFB, and the DPL appear to be better than $CR_m$s of images reconstructed according to the GF. The DPL has better performance on the $CR_m$ than the GF, the DLU, and the DLFB. The GF has poorer performance on the RCR than the DLU, the DLFB, and the DPL.

FIG. 11 illustrates images of the Hoffman brain phantom reconstructed based on scanning data corresponding to different scanning time periods according to different approaches according to some embodiments of the present disclosure. As shown in FIG. 11, images reconstructed, based on scanning data corresponding to a same scanning time period, according to the DLU, the DLFB, and the DPL appear to have better image quality than images reconstructed according to the GF. In addition, the image quality of images reconstructed based on scanning data corresponding to a scanning time period of 1 minute according to the DLU, the DLFB, and the DPL appear to be close to or better than the image quality of images reconstructed based on scanning data (e.g., full data) corresponding to a scanning time period of 10 minutes according to the GF.

FIG. 12 illustrates images of a patient reconstructed based on full data and fast scan data according to different approaches according to some embodiments of the present disclosure.

The patient was injected with F18-FDG of 279 MBq and scanned for 180 seconds per bed position (s/bp). Scanning data (e.g., in the form of listmode data, also referred to as full data) of the patient were down-sampled to 60 s/bp to simulate fast scan data. Images (e.g., maximum intensity projection images) of the patient may be reconstructed based on the fast scan data and the full data according to different approaches. The different approaches (e.g., the GF, the DLU, the DLFB, and the DPL) and settings (e.g., a network architecture, a reconstruction algorithm, an image correction operation, etc.) of networks of the different approaches may be the same as the approaches and corresponding settings exemplified above.

As shown in FIG. 12, imaging quality of small lesions (e.g., the small lesions marked using arrows in the upper left image) in images reconstructed according to the DLU, the DLFB, and the DPL appear to be better than imaging quality of small lesions in images reconstructed according to the GF. To quantitatively evaluate the performance of small lesion detection of the different approaches, maximum standardized uptake values ($SUV_{max}$s) and CNRs of ten lesions were obtained. FIG. 13 illustrates $SUV_{max}$s and CNRs of the lesions in images reconstructed based on full data and fast scan data according to the different approaches according to some embodiments of the present disclosure. Bars and error bars shown in FIG. 13 denote mean values and 1 SD, respectively. For the simulated 60 s/bp scan, an averaged SUV. (CNR) for the GF, the DLU, the DLFB, and the DPL were 3.52(8.68), 4.33(30.9), 5.32(31.3) and 6.46(32.3), respectively. For the 180 s/bp scan, an averaged SUV. (CNR) for the GF, the DLU, the DLFB, and the DPL were 3.26(15.5), 3.98(49.7), 4.85(48.5), and 6.13(55.7), respectively. According to FIG. 13, the $SUV_{max}$s and CNRs of the lesions in images reconstructed according to the DLU, the DLFB, and the DPL appear to be better than the SUVs and CNRs of the lesions in images reconstructed according to the GF, respectively.

Having thus described the basic concepts, it may be rather apparent to those skilled in the art after reading this detailed disclosure that the foregoing detailed disclosure is intended to be presented by way of example only and is not limiting.

Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system, comprising:
   at least one storage medium including a set of instructions; and
   at least one processor configured to communicate with the at least one storage medium, wherein when executing the set of instructions, the at least one processor is configured to direct the system to perform operations including:
   obtaining a machine learning model and preliminary training data of at least one sample subject, the preliminary training data being acquired using a first positron emission tomography (PET) scanner;
   generating training input data by processing the preliminary training data, the preliminary training data being superior to the training input data with respect to a data quality parameter, the training input data being configured to simulate first scanning data acquired using a second PET scanner, the first PET scanner being with a higher PET imaging performance than the second PET scanner; and
   determining a trained machine learning model by training the machine learning model based on the training input data and the preliminary training data, the preliminary training data being configured as a ground truth for training the machine learning model, the trained machine learning model being configured to optimize second scanning data acquired using the second PET scanner.

2. The system of claim 1, wherein the preliminary training data includes at least one of raw data obtained from the first PET scanner, sinogram data corresponding to the raw data, or image data reconstructed based on the raw data.

3. The system of claim 1, wherein the data quality parameter includes at least one of a signal-to-noise ratio (SNR), a spatial resolution, or an image contrast.

4. The system of claim 1, wherein the preliminary training data is processed by performing at least one of a data splitting operation, a data rebinning operation, or a down-sampling operation.

5. The system of claim 1, wherein the preliminary training data includes third first scanning data generated by the first PET scanner having a larger axial length than the second PET scanner.

6. The system of claim 5, wherein the generating training input data by processing the preliminary training data includes:
   down-sampling the third first scanning data at a preset down-sampling rate; and
   designating the down-sampled third first scanning data as the training input data.

7. The system of claim 1, wherein the preliminary training data includes first listmode data generated by the first PET scanner having a higher time of flight (TOF) resolution than the second PET scanner.

8. The system of claim 7, wherein the generating training input data by processing the preliminary training data includes:
   rebinning the first listmode data according to preset TOF information; and
   designating the rebinned first listmode data as the training input data.

9. The system of claim 1, wherein the preliminary training data includes second listmode data generated by the first PET scanner having a smaller detector unit size than the second PET scanner.

10. The system of claim 9, wherein the generating training input data by processing the preliminary training data includes:
    determining coordinates of virtual detector units based on coordinates of detector units of the first PET scanner and a preset detector unit size, the preset detector unit size being larger than the detector unit size of the first PET scanner;
    rebinning the second listmode data according to the determined coordinates of the virtual detector units; and
    designating the rebinned second listmode data as the training input data.

11. The system of claim 1, wherein preliminary training data includes third listmode data generated by the first PET scanner having a higher noise equivalent count rate (NECR) than the second PET scanner.

12. The system of claim 11, wherein the generating training input data by processing the preliminary training data includes:
    extracting a data set from delayed coincidence counts of the third listmode data;
    generating two data sets by duplicating the data set, wherein coincidence marks of one data set remain unchanged, and coincidence marks of the other data set are replaced with prompt coincidence counts;
    generating fourth listmode data by incorporating the two data sets into the third listmode data; and
    designating the fourth listmode data as the training input data.

13. The system of claim 1, wherein the preliminary training data includes first listmode data generated by the first PET scanner having a higher time of flight (TOF) resolution than the second PET scanner.

14. A system, comprising:
    at least one storage medium including a set of instructions; and
    at least one processor configured to communicate with the at least one storage medium, wherein when executing the set of instructions, the at least one processor is configured to direct the system to perform operations including:
    obtaining a trained machine learning model, wherein the trained machine learning model is trained using training data that includes preliminary training data and training input data, wherein the preliminary training data is acquired by scanning at least one sample subject using a first positron emission tomography (PET) scanner, the training input data is generated by processing the preliminary training data, the preliminary training data is superior to the training input data with respect to a data quality parameter, the training input data is configured to simulate first scanning data acquired using a second PET scanner, the first PET scanner is with a higher PET imaging performance than the second PET scanner, and the preliminary training data is configured as a ground truth for obtaining the machine learning model;

obtaining scanning data of a subject acquired by scanning the subject using the second PET scanner; and generating optimized scanning data of the subject by inputting the scanning data into the trained machine learning.

15. A method implemented on a computing device having a processor and a computer-readable storage device, the method comprising:

obtaining a machine learning model and preliminary training data of at least one sample subject, the preliminary training data being acquired using a first positron emission tomography (PET) scanner;

generating training input data by processing the preliminary training data, the preliminary training data being superior to the training input data with respect to a data quality parameter, the training input data being configured to simulate first scanning data acquired using a second PET scanner, the first PET scanner being with a higher PET imaging performance than the second PET scanner; and determining a trained machine learning model by training the machine learning model based on the training input data and the preliminary training data, the preliminary training data being configured as a ground truth for training the machine learning model, the trained machine learning model being configured to optimize second scanning data acquired using the second PET scanner.

16. The method of claim 15, wherein the preliminary training data includes at least one of raw data obtained from the first PET scanner, sinogram data corresponding to the raw data, or image data reconstructed based on the raw data.

17. The method of claim 15, wherein the data quality parameter includes at least one of a signal-to-noise ratio (SNR), a spatial resolution, or an image contrast.

18. The method of claim 15, wherein the preliminary training data is processed by performing at least one of a data splitting operation, a data rebinning operation, or a down-sampling operation.

19. The method of claim 15, wherein the preliminary training data includes third scanning data generated by the first PET scanner having a larger axial length than the second PET scanner.

20. The method of claim 19, wherein the generating training input data by processing the preliminary training data includes:

down-sampling the third scanning data at a preset down-sampling rate; and designating the down-sampled third scanning data as the training input data.

*     *     *     *     *